(12) United States Patent
Forneris et al.

(10) Patent No.: US 12,150,788 B2
(45) Date of Patent: Nov. 26, 2024

(54) METHOD AND SYSTEM FOR DETERMINING REGIONAL RUPTURE POTENTIAL OF BLOOD VESSEL

(71) Applicant: VITAA MEDICAL SOLUTIONS INC., Montréal (CA)

(72) Inventors: Arianna Forneris, Alberta (CA); Randy D. Moore, Alberta (CA); Elena Di Martino, Alberta (CA)

(73) Assignee: ViTAA Medical Solutions, Montréal (CA)

( * ) Notice: Subject to any disclaimer, the term of this patent is extended or adjusted under 35 U.S.C. 154(b) by 161 days.

(21) Appl. No.: 17/763,594

(22) PCT Filed: Sep. 25, 2020

(86) PCT No.: PCT/IB2020/059018
§ 371 (c)(1),
(2) Date: Mar. 24, 2022

(87) PCT Pub. No.: WO2021/059243
PCT Pub. Date: Apr. 1, 2021

(65) Prior Publication Data
US 2022/0330902 A1 Oct. 20, 2022

Related U.S. Application Data

(60) Provisional application No. 62/906,980, filed on Sep. 27, 2019.

(51) Int. Cl.
*A61B 5/00* (2006.01)
*A61B 5/02* (2006.01)
(Continued)

(52) U.S. Cl.
CPC ........ *A61B 5/7275* (2013.01); *A61B 5/02014* (2013.01); *A61B 5/0263* (2013.01);
(Continued)

(58) Field of Classification Search
CPC ... A61B 5/7275; A61B 5/02014; A61B 5/026; G16H 50/30; G06T 2207/30104
See application file for complete search history.

(56) References Cited

U.S. PATENT DOCUMENTS

2005/0033409 A1 2/2005 Burke
2006/0149522 A1 7/2006 Tang
(Continued)

FOREIGN PATENT DOCUMENTS

JP 2008503302 2/2008
JP 2008510499 4/2008
(Continued)

OTHER PUBLICATIONS

D. Vorp et al, "Mechanical wall stress in abdominal aortic aneurysm: Influence of diameter and asymmetry", Journal of Vascular Surgery, vol. 27, No. 4, pp. 632-639, Apr. 1998 (Year: 1998).*
(Continued)

*Primary Examiner* — Joel Lamprecht
*Assistant Examiner* — Nyrobi Celestine
(74) *Attorney, Agent, or Firm* — Blueshift IP; Robert Plotkin

(57) ABSTRACT

There is provided a method for determining a regional rupture potential (RRP) indicative of the state of local weakening of a blood vessel based on parameters that correlate with the expansion and local weakening of the vessel. The method comprises: receiving a plurality of images of the blood vessel into a multiphase stack. A geometrical model of the lumen and the outer wall of the vessel are generated and smoothed to obtain a volume mesh and surface mesh respectively. An ILT thickness distribution, a local deformation at each phase and a wall strain distribution indicative of a maximal principal strain at the outer wall are determined. Blood flow values in the lumen
(Continued)

are obtained and a wall shear stress distribution indicative of wall shear disturbances in the lumen is calculated. The RRP is determined based on the ILT thickness distribution, the wall shear stress, and the wall strain.

20 Claims, 11 Drawing Sheets

(51) Int. Cl.
    *A61B 5/026*     (2006.01)
    *G06T 7/00*     (2017.01)
    *G16H 30/40*     (2018.01)
    *G16H 50/50*     (2018.01)
(52) U.S. Cl.
    CPC .......... *G06T 7/0012* (2013.01); *G16H 30/40* (2018.01); *G16H 50/50* (2018.01); *G06T 2207/30104* (2013.01)

(56) References Cited

U.S. PATENT DOCUMENTS

| | | | |
|---|---|---|---|
| 2008/0137929 | A1 | 6/2008 | Chen |
| 2010/0284587 | A1* | 11/2010 | Malek ................ A61B 5/02014 382/128 |
| 2012/0041318 | A1 | 2/2012 | Taylor |
| 2014/0355851 | A1* | 12/2014 | Gasser ................ G06T 7/0012 382/128 |
| 2015/0095282 | A1 | 4/2015 | Jones |
| 2017/0347966 | A1* | 12/2017 | Yagi ........................ G16H 50/50 |
| 2020/0188029 | A1* | 6/2020 | Taylor .................... A61B 5/029 |
| 2022/0406470 | A1* | 12/2022 | Fonte .................... A61B 5/0044 |

FOREIGN PATENT DOCUMENTS

| | | |
|---|---|---|
| JP | 2013534154 | 9/2013 |
| JP | 2018000981 | 1/2018 |
| WO | 2017047822 | 3/2017 |
| WO | 2018068153 A1 | 4/2018 |
| WO | 2018141628 A1 | 8/2018 |

OTHER PUBLICATIONS

M. Raghavan et al, "Wall stress distribution on three-dimensionally reconstructed models of human abdominal aortic aneurysm", Journal of Vascular Surgery, vol. 31, No. 4, pp. 760-769, Apr. 2000 (Year: 2000).*
M. Raghavan et al, "Toward a biomechanical tool to evaluate rupture potential of abdominal aortic aneurysm: identification of a finite strain constitutive model and evaluation of its applicability", Journal of Biomechanics, vol. 33, pp. 475-482, 2000 (Year: 2000).*
J. Geest et al, "A Biomechanics-Based Rupture Potential Index for Abdominal Aortic Aneurysm Risk Assessment", Annals New York Academy of Sciences, vol. 1085, pp. 11-21, 2006 (Year: 2006).*
L. Boussel et al, "Aneurysm Growth Occurs at Region of Low Wall Shear Stress Patient-Specific Correlation of Hemodynamics and Growth in a Longitudinal Study", Stroke, vol. 39, No. 11, pp. 2997-3002, Nov. 2008 (Year: 2008).*
A. Maier et al, "A Comparison of Diameter, Wall Stress, and Rupture Potential Index for Abdominal Aortic Aneurysm Rupture Risk Prediction", Annals of Biomedical Engineering, vol. 38, No. 10, pp. 3124-3134, Oct. 2010 (Year: 2010).*
F. Riveros et al, "Influence of Intraluminal Thrombus Topology on AAA Passive Mechanics", Computing in Cardiology, vol. 40, pp. 899-902, 2013 (Year: 2013).*
H. Zhang et al, "Robust infrarenal aortic aneurysm lumen centerline detection for rupture status classification", Medical Engineering and Physics, vol. 35, pp. 1358-1367, Mar. 2013 (Year: 2013).*
P. Achille et al, "A haemodynamic predictor of intraluminal thrombus formation in abdominal aortic aneurysms", Proceedings of the Royal Society, vol. 470, pp. 1-22, Aug. 2014 (Year: 2014).*
J. Cebral et al, "Wall Mechanical Properties and Hemodynamics of Unruptured Intracranial Aneurysms", American Journal of Neuroradiology, vol. 36, No. 9, pp. 1695-1703, Sep. 2015 (Year: 2015).*
A. Boyd et al, "Low wall shear stress predominates at sites of abdominal aortic aneurysm rupture", Journal of Vascular Surgery, vol. 63, No. 6, pp. 1613-1619, Jun. 2016 (Year: 2016).*
G. Zhou et al, "Association of wall shear stress with intracranial aneurysm rupture: systematic review and metaanalysis", Scientific Reports, vol. 7, pp. 1-8, Jul. 2017 (Year: 2017).*
Z. Wang et al, "Impact of Patient-Specific Material Properties on Aneurysm Wall Stress: Finite Element Study", The Journal of Heart Valve Disease, vol. 27, No. 5, pp. 275-284, 2018 (Year: 2018).*
S. Raut et al, "An Approach for Patient-Specific Multi-domain Vascular Mesh Generation Featuring Spatially Varying Wall Thickness Modeling", Journal of Biomechanics, vol. 48, No. 10, pp. 1972-1981, Jul. 2015 (Year: 2015).*
Extended European Search Report issued in App. No. EP20869172, dated Sep. 25, 2023, 15 pages.
International Search Report and Written Opinion mailed Jan. 5, 2021, in International Patent Application No. PCT/IB2020/059018, 5 pages.
Arianna Forneris et al., "A novel combined fluid dynamic and strain analysis approach identified abdominal aortic aneurysm rupture," Journal of Vascular Surgery Cases and Innovative Techniques, Jun. 2020, vol. 6(2), pp. 172-176. Retrieved from the Internet Dec. 16, 2020: https://www.sciencedirect.com/science/article/pii/S2468428720300149.
Giampaolo Martufi et al., "Three-dimensional geometrical characterization of abdominal aortic aneurysms: image-based wall thickness distribution," Journal of Biomechanical Engineering, Jun. 2009; vol. 131(6), pp. 1-11. Retrieved from the internet https://pubmed.ncbi.nlm.nih.gov/19449969/.
Wolters et al., "A patient-specific computational model of fluid-structure interaction in abdominal aortic aneurysms," Medical Engineering Physics, Dec. 2005, vol. 27, Issue 10, pp. 871-883.
Japanese Office Action issued in App. No. JP2022519808, dated Oct. 1, 2024, 4 pages.

* cited by examiner

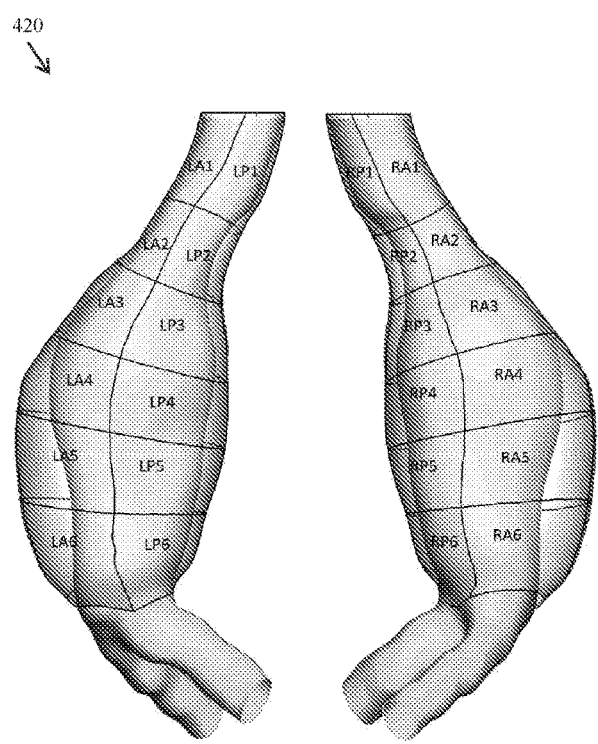
Figure 4A
Figure 4B

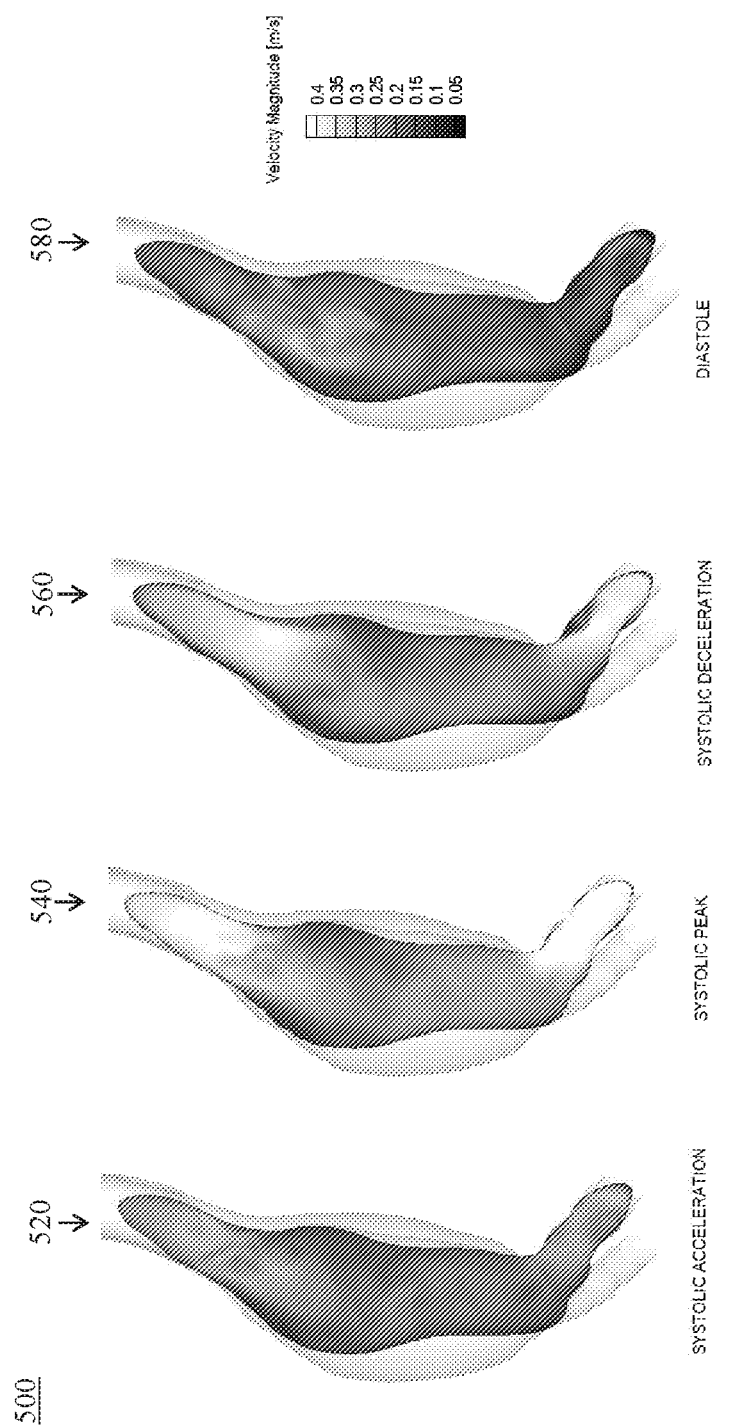

METHOD AND SYSTEM FOR DETERMINING REGIONAL RUPTURE POTENTIAL OF BLOOD VESSEL

FIELD

The present technology relates to the field of biomedical imaging in general and more specifically to a method and a system for determining weakening and consequent expansion and rupture potential in regions of an aneurysm in a blood vessel.

BACKGROUND

Aortic aneurysms (abdominal and thoracic) are generally asymptomatic and indolent. If left untreated, an aneurysm will gradually expand until rupture, an event that carries a mortality rate of 90%.

Clinical management of aortic aneurysm relies on the assessment of the maximum aortic diameter as marker of rupture risk. A significant individual variability, however, has been reported as demonstration of the poor predictive potential of the vessel's maximum diameter.

Local hemodynamic forces are known to have a crucial role in regulating vascular function as well as promoting local structural remodeling in response to long-term flow alterations expansion. However, a clear insight on the localized weakening of the aortic wall has yet to be found.

SUMMARY

It is an object of the present technology to ameliorate at least some of the inconveniences present in the prior art. Embodiments of the present technology may provide and/or broaden the scope of approaches to and/or methods of achieving the aims and objects of the present technology.

Embodiments of the present technology enable estimating in vivo rupture potential of an aneurysm in a blood vessel by using 3D models of the blood vessel and computational fluid dynamics simulations and determining local properties and hemodynamic indices. More specifically, the present technology enables assessment of individual aortas based on parameters that correlate with the local weakening, expansion and rupture of the vessel and provides a rationale for clinical decisions by performing calculations solely based on images acquired by a medical imaging apparatus.

Embodiments of the present technology have been developed based on developers' appreciation that local hemodynamic forces are known to have a crucial role in regulating vascular function as well as promoting local structural remodeling in response to long-term flow alterations. Aortic expansion and rupture have been associated to regions of low wall shear stress (WSS) load (<0.4 Pa) and intraluminal thrombus (ILT) accumulation.

More specifically, based on the above, developers of the present technology have realized that a clear insight on the weakening of the aortic wall has yet to be found.

The present technology determines the deformability of aortic aneurysm through in vivo strain measurements, as it relates to local mechanical properties and aortic function, and correlates the state of weakening of the aorta with local deformation, local intraluminal thrombus (ILT) thickness and hemodynamic indices obtained via a computational fluid dynamic (CFD) simulation or, alternatively, via 4D-flow MRI data for a given patient. In one embodiment, the results are combined to obtain a regional rupture potential (RRP) indicative of a state of weakening and rupture probability of a given region.

Thus, embodiments of the present technology are directed to a method and a system for determining regional rupture potential indicative of a state of local weakening of a blood vessel based on the parameters that correlate with local weakening, expansion and rupture of the vessel's wall.

In accordance with a broad aspect of the present technology, there is provided a computer-implemented method for determining a rupture potential of at least one region of a blood vessel of a given subject, the method being executable by a server, the method comprising: receiving, by the server, a plurality of images of the blood vessel of the given subject, the plurality of images having been acquired by a medical imaging apparatus. The method comprises organizing, by the server, the plurality of images into a multiphase stack, a given phase of the multiphase stack being representative of the blood vessel at a given time in a cardiac cycle. The method further comprises generating, by the server, a volume mesh of a lumen of the blood vessel and a surface mesh of an outer wall of the blood, using the multiphase stack; calculating, by the server, based on the surface mesh of the lumen and the surface mesh of the outer wall, a thickness parameter; determining, by the server, a local deformation at each phase of the multiphase stack by mapping voxels of the surface mesh of the outer wall to the multiphase stack; calculating, by the server, based on the local deformation at each phase, a wall strain parameter indicative of a maximum principal strain at the outer wall; generating a blood flow parameter based at least in part on the volume mesh of the lumen, the blood flow parameter comprising a respective set of blood flow values in the lumen for a cardiac cycle; calculating, by the server, based on the blood flow parameter, a wall shear stress parameter indicative of wall shear disturbances in the lumen; and determining, by the server, based on the thickness parameter, the wall strain parameter, and the wall shear stress parameter, a rupture potential parameter of the blood vessel, the rupture potential parameter being indicative of a state of weakening of the at least one region of the blood vessel.

In some embodiment, the step of generating the volume mesh of the lumen and said generating the surface mesh of the outer wall comprise: generating, by the server, a first geometrical model of the lumen of the blood vessel and a second geometrical model of the outer wall of the blood vessel by segmenting the multiphase stack; and smoothing, by the server, the first geometrical model to obtain the volume mesh of the lumen, and the second geometrical model to obtain the surface mesh of the outer wall.

In some embodiments of the method, at least one wall shear stress parameter comprises a time averaged wall-shear stress (TAWSS).

In some embodiments of the method, the generating the blood flow parameter comprises generating a computational flow dynamic (CFD) simulation of blood flow in the lumen to obtain the respective set of blood flow values in the lumen for the cardiac cycle.

In some embodiments of the method, the generating the blood flow parameter comprises performing a 4D-flow MRI acquisition to obtain the respective set of blood flow values in the lumen for the cardiac cycle.

In some embodiments of the method, the method further comprises, prior to calculating the wall strain parameter: determining, based on the multiphase stack and the surface mesh of the outer wall, a local deformation at each phase of the surface mesh, and the calculating the wall strain parameter is based on the local deformation at each phase of the surface mesh.

In some embodiments of the method, the calculating the thickness parameter comprises calculating an intraluminal thrombus (ILT) thickness based on: a distance between the surface mesh of the outer wall and a surface mesh of the lumen.

In some embodiments of the method, the method further comprises, prior to the determining the rupture potential parameter: receiving a population-based thickness parameter, a population-based wall strain parameter, and a population-based wall shear stress parameter, and the determining the rupture potential parameter is further based on the population-based thickness parameter, the population-based wall strain parameter, and the population-based wall shear stress parameter.

In some embodiments of the method, the method further comprises, prior to the estimating the rupture potential parameter: defining, by the server, a plurality of patches on the blood vessel. The calculating the thickness parameter, the wall strain parameter, and the wall shear stress parameter, comprises calculating a patch-averaged thickness parameter, a patch-averaged wall strain parameter and a patch-averaged wall shear stress parameter using the plurality of patches, and the rupture potential parameter is based on the patch-averaged thickness parameter, the patch-averaged wall strain parameter and the patch-averaged wall shear stress parameter.

In some embodiments of the method, the calculating the patch-averaged thickness parameter, the patch-averaged wall strain parameter and the patch-averaged wall shear stress parameter is further based on the population-based thickness parameter, the population-based wall strain parameter, and the population-based wall shear stress parameter.

In some embodiments of the method, the method further comprises determining respective distribution quartiles for each of the patch-averaged thickness parameter, the patch-averaged wall strain parameter and the patch-averaged wall shear stress parameter.

In some embodiments of the method, further comprising classifying each of the patch-averaged thickness parameter, the patch-averaged wall strain parameter and the patch-averaged wall shear stress parameter based on the respective distribution quartiles.

In some embodiments of the method, the rupture potential parameter is determined based on:

$$\frac{[ILT_{category} + STRAIN_{category} + (5 - TAWSS_{category})] - 3}{9} \cdot 100$$

where $ILT_{category}$ is a respective category assigned to the thickness parameter, $STRAIN_{category}$ is a respective category assigned to the wall strain parameter, and $TAWSS_{category}$ is a respective category assigned to the wall shear stress parameter.

In some embodiments of the method, the respective categories have respective values between 1 and 4.

In accordance with another broad aspect of the present technology, there is provided a system for determining a rupture potential indicative of a state of local weakening of at least one region of a blood vessel of a given subject, the system comprising: a processor, a computer-readable storage medium connected to the processor, the computer-readable storage medium including instructions, the processor, upon executing the instructions, being configured for: receiving a plurality of images of the blood vessel of the given subject, the plurality of images having been acquired by a medical imaging apparatus. The processor is configured for organizing the plurality of images into a multiphase stack, a given phase of the multiphase stack being representative of the blood vessel at a given time in a cardiac cycle. The processor is configured for generating a volume mesh of a lumen of the blood vessel and a surface mesh of an outer wall of the blood, using the multiphase stack; calculating based on the volume mesh of the lumen and the surface mesh of the outer wall, a thickness parameter; determining a local deformation at each phase of the multiphase stack by mapping voxels of the surface mesh of the outer wall to the multiphase stack; calculating based on the local deformation at each phase, a wall strain parameter indicative of a maximum principal strain at the outer wall; generating a blood flow parameter based at least in part on the volume mesh of the lumen, the blood flow parameter comprising a respective set of blood flow values in the lumen for a given moment in time; calculating based on the blood flow parameter, a wall shear stress parameter indicative of wall shear disturbances in the lumen; determining based on the lumen thickness parameter, the wall strain parameter, and the wall shear stress parameter, a rupture potential parameter of the blood vessel, the rupture potential parameter being indicative of a state of weakening of at least one region of the blood vessel.

In some embodiments, the generating the volume mesh of the lumen and said generating the surface mesh of the outer wall comprise: generating, by the server, a first geometrical model of the lumen of the blood vessel and a second geometrical model of the outer wall of the blood vessel by segmenting the multiphase stack; and smoothing, by the server, the first geometrical model to obtain the volume mesh of the lumen, and the second geometrical model to obtain the surface mesh of the outer wall.

In some embodiments of the system, at least one wall shear stress parameter comprises a time averaged wall-shear stress.

In some embodiments of the system, the generating the blood flow parameter comprises generating a computational fluid dynamic simulation of blood flow in the lumen to obtain the respective set of blood flow values in the lumen for the cardiac cycle.

In some embodiments of the system, the generating the blood flow parameter comprises performing a 4D-flow MRI acquisition to obtain the respective set of blood flow values in the lumen for the cardiac cycle.

In some embodiments of the system, the processor is further configured for, prior to the calculating the wall strain parameter: determining, based on the multiphase stack and the surface mesh of the outer wall, a local deformation of the surface mesh at each phase of the multiphase stack, and the calculating the wall strain parameter is based on the local deformation at each phase of the surface mesh.

In some embodiments of the system, the thickness parameter is determined based on: a distance between the surface mesh of the outer wall and the surface of the lumen.

In some embodiments of the system, the processor is further configured for, prior to the determining the regional rupture potential parameter: receiving a population-based thickness parameter, a population-based wall strain parameter, and a population-based wall shear stress parameter. The determining the regional rupture potential parameter is further based on the population-based thickness parameter, the population-based wall strain parameter, and the population-based wall shear stress parameter.

In some embodiments of the system, the processor is further configured for, prior to the estimating the rupture potential parameter: defining a plurality of patches on the blood vessel, the step of calculating the thickness parameter, the wall strain parameter, and the wall shear stress parameter comprises calculating a patch-averaged thickness parameter, a patch-averaged wall strain parameter and a patch-averaged wall shear stress parameter using the plurality of patches, and the regional rupture potential parameter is based on the patch-averaged thickness parameter, the patch-averaged wall strain parameter and the patch-averaged wall shear stress parameter.

In some embodiments of the system, the calculating the patch-averaged thickness parameter, the patch-averaged wall strain parameter and the patch-averaged wall shear stress parameter is further based on the population-based thickness parameter, the population-based wall strain parameter, and the population-based wall shear stress parameter.

In some embodiments of the system, the processor is further configured for determining respective distribution quartiles for each of the patch-averaged thickness parameter, the patch-averaged wall strain parameter and the patch-averaged wall shear stress parameter.

In some embodiments of the system, the processor is further configured for classifying each of the patch-averaged thickness parameter, the patch-averaged wall strain parameter and the patch-averaged wall shear stress parameter based on the respective distribution quartiles.

In some embodiments of the system, the rupture potential parameter is determined based on:

$$\frac{[ILT_{category} + STRAIN_{category} + (5 - TAWSS_{category})] - 3}{9} \cdot 100$$

where $ILT_{category}$ is a respective category assigned to the thickness parameter,
$STRAIN_{category}$ is a respective category assigned to the wall strain parameter, and
$TAWSS_{category}$ is a respective category assigned to the wall shear stress parameter.

In some embodiments of the system, the respective categories have respective values between 1 and 4.

Definitions

In the context of the present specification, a "server" is a computer program that is running on appropriate hardware and is capable of receiving requests (e.g., from electronic devices) over a network (e.g., a communication network), and carrying out those requests, or causing those requests to be carried out. The hardware may be one physical computer or one physical computer system, but neither is required to be the case with respect to the present technology. In the present context, the use of the expression "a server" is not intended to mean that every task (e.g., received instructions or requests) or any particular task will have been received, carried out, or caused to be carried out, by the same server (i.e., the same software and/or hardware); it is intended to mean that any number of software elements or hardware devices may be involved in receiving/sending, carrying out or causing to be carried out any task or request, or the consequences of any task or request; and all of this software and hardware may be one server or multiple servers, both of which are included within the expressions "at least one server" and "a server".

In the context of the present specification, "electronic device" is any computing apparatus or computer hardware that is capable of running software appropriate to the relevant task at hand. Thus, some (non-limiting) examples of electronic devices include general purpose personal computers (desktops, laptops, netbooks, etc.), mobile computing devices, smartphones, and tablets, and network equipment such as routers, switches, and gateways. It should be noted that an electronic device in the present context is not precluded from acting as a server to other electronic devices. The use of the expression "an electronic device" does not preclude multiple electronic devices being used in receiving/sending, carrying out or causing to be carried out any task or request, or the consequences of any task or request, or steps of any method described herein. In the context of the present specification, a "client device" refers to any of a range of end-user client electronic devices, associated with a user, such as personal computers, tablets, smartphones, and the like.

In the context of the present specification, the expression "computer readable storage medium" (also referred to as "storage medium" and "storage") is intended to include non-transitory media of any nature and kind whatsoever, including without limitation RAM, ROM, disks (CD-ROMs, DVDs, floppy disks, hard drivers, etc.), USB keys, solid state-drives, tape drives, etc. A plurality of components may be combined to form the computer information storage media, including two or more media components of a same type and/or two or more media components of different types.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, the expression "information" includes information of any nature or kind whatsoever capable of being stored in a database. Thus, information includes, but is not limited to audiovisual works (images, movies, sound records, presentations etc.), data (location data, numerical data, etc.), text (opinions, comments, questions, messages, etc.), documents, spreadsheets, lists of words, etc.

In the context of the present specification, unless expressly provided otherwise, an "indication" of an information element may be the information element itself or a pointer, reference, link, or other indirect mechanism enabling the recipient of the indication to locate a network, memory, database, or other computer-readable medium location from which the information element may be retrieved. For example, an indication of a document could include the document itself (i.e. its contents), or it could be a unique document descriptor identifying a file with respect to a particular file system, or some other means of directing the recipient of the indication to a network location, memory address, database table, or other location where the file may be accessed. As one skilled in the art would recognize, the degree of precision required in such an indication depends on the extent of any prior understanding about the interpretation to be given to information being exchanged as between the sender and the recipient of the indication. For example, if it is understood prior to a communication between a sender and a recipient that an indication of an information element will take the form of a database key for an entry in a particular table of a predetermined database containing the information element, then the sending of the database key is all that is required to effectively convey the information element to the recipient, even though the information element itself was not transmitted as between the sender and the recipient of the indication.

In the context of the present specification, the expression "communication network" is intended to include a telecommunications network such as a computer network, the Internet, a telephone network, a Telex network, a TCP/IP data network (e.g., a WAN network, a LAN network, etc.), and the like. The term "communication network" includes a wired network or direct-wired connection, and wireless media such as acoustic, radio frequency (RF), infrared and other wireless media, as well as combinations of any of the above.

In the context of the present specification, the expression "parameter" is intended to include numerical representations of characteristics of a system. A parameter may be measured, or may be calculated. A parameter may include a single value or a plurality of values, and may be represented as a vector, a matrix, and a tensor. As a non-limiting example, a parameter may represent a single numerical value, a frequency distribution, and a probability distribution.

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "server" and "third server" is not intended to imply any particular order, type, chronology, hierarchy or ranking (for example) of/between the servers, nor is their use (by itself) intended to imply that any "second server" must necessarily exist in any given situation. Further, as is discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

Implementations of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where:

FIG. 4A illustrates a 3D geometrical model of an outer wall and a lumen of an abdominal aortic aneurysm (AAA) with twenty-four patches in accordance with non-limiting embodiments of the present technology.

FIG. 4B illustrates a left sagittal oblique view of cardiac gated CT scan demonstrating a site of contained aortic rupture at left posterolateral portion of an aortic wall confirmed during subsequent surgery in accordance with non-limiting embodiment of the present technology.

FIG. 5 illustrates computational fluid dynamics predicted velocity contours on a longitudinal cross section of the AAA at different times of the cardiac cycle in accordance with non-limiting embodiments of the present technology.

DETAILED DESCRIPTION

Figure 1:
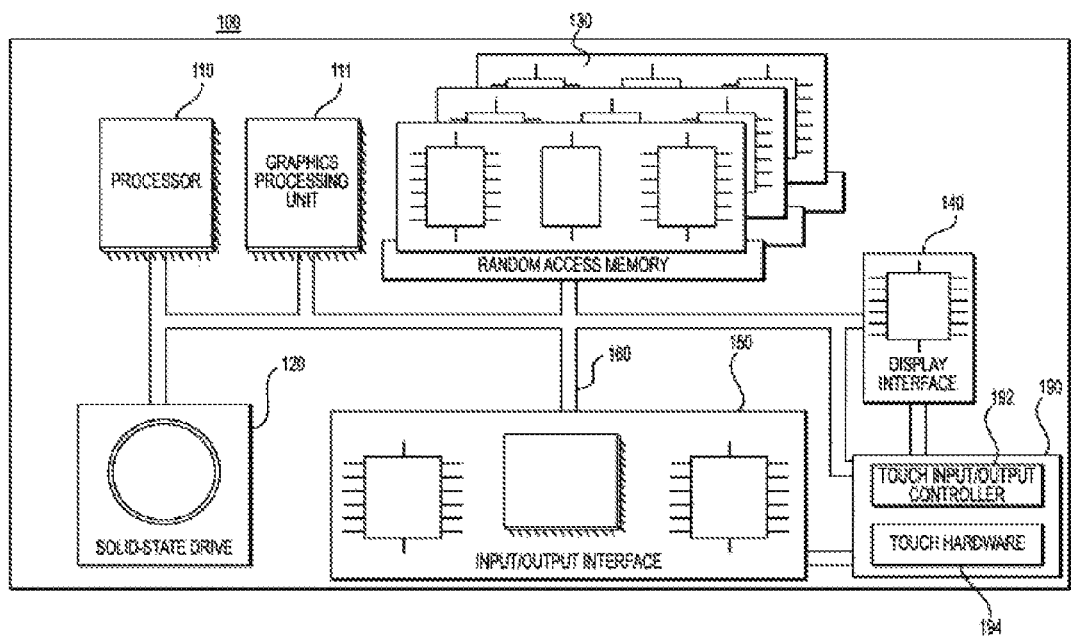
FIG. 1 depicts a schematic diagram of an electronic device in accordance with non-limiting embodiments of the present technology.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudocode, and the like represent various processes which may be substantially represented in computer-readable media and so executed by a computer or processor, whether or not such computer or processor is explicitly shown.

The functions of the various elements shown in the figures, including any functional block labeled as a "processor" or a "graphics processing unit", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some non-limiting embodiments of the present technology, the processor may be a general purpose processor, such as a central processing unit (CPU) or a processor dedicated to a specific purpose, such as a graphics processing unit (GPU). Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RANI), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

With these fundamentals in place, we will now consider some non-limiting examples to illustrate various implementations of aspects of the present technology.

With reference to FIG. 1, there is depicted a schematic diagram of an electronic device 100 suitable for use with some non-limiting embodiments of the present technology.
Electronic Device The electronic device 100 comprises various hardware components including one or more single or multi-core processors collectively represented by processor 110, a graphics processing unit (GPU) 111, a solid-state drive 120, a random access memory 130, a display interface 140, and an input/output interface 150.

Communication between the various components of the electronic device 100 may be enabled by one or more internal and/or external buses 160 (e.g. a PCI bus, universal serial bus, IEEE 1394 "Firewire" bus, SCSI bus, Serial-ATA bus, etc.), to which the various hardware components are electronically coupled.

The input/output interface 150 may be coupled to a touchscreen 190 and/or to the one or more internal and/or external buses 160. The touchscreen 190 may be part of the display. In some embodiments, the touchscreen 190 is the display. The touchscreen 190 may equally be referred to as a screen 190. In the embodiments illustrated in FIG. 1, the touchscreen 190 comprises touch hardware 194 (e.g., pressure-sensitive cells embedded in a layer of a display allowing detection of a physical interaction between a user and the display) and a touch input/output controller 192 allowing communication with the display interface 140 and/or the one or more internal and/or external buses 160. In some embodiments, the input/output interface 150 may be connected to a keyboard (not shown), a mouse (not shown) or a trackpad (not shown) allowing the user to interact with the electronic device 100 in addition or in replacement of the touchscreen 190.

According to implementations of the present technology, the solid-state drive 120 stores program instructions suitable for being loaded into the random access memory 130 and executed by the processor 110 and/or the GPU 111 for estimating a rupture potential of a blood vessel of a given subject. For example, the program instructions may be part of a library or an application.

The electronic device 100 may be implemented in the form of a server, a desktop computer, a laptop computer, a tablet, a smartphone, a personal digital assistant or any device that may be configured to implement the present technology, as it may be understood by a person skilled in the art.
System Referring to FIG. 2, there is shown a schematic diagram of a system 200, the system 200 being suitable for implementing non-limiting embodiments of the present technology. It is to be expressly understood that the system 200 as depicted is merely an illustrative implementation of the present technology. Thus, the description thereof that follows is intended to be only a description of illustrative examples of the present technology. This description is not intended to define the scope or set forth the bounds of the present technology. In some cases, what are believed to be helpful examples of modifications to the system 200 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition it is to be understood that the system 200 may provide in certain instances simple implementations of the present technology, and that where such is the case they have been presented in this manner as an aid to understanding. As persons skilled in the art would understand, various implementations of the present technology may be of a greater complexity.

The system 200 comprises inter alia a medical imaging apparatus 210 associated with a workstation computer 215, and a server 230 coupled over a communications network 220 via respective communication links 225.
Medical Device Generally speaking, the medical imaging apparatus 210 is configured to acquire, at different time points, a plurality of images of a blood vessel of a given subject such that a representation of the blood vessel of the given subject may be subsequently generated. In one embodiment, the medical imaging apparatus 210 is configured to acquire electrocardiographically (ECG)-gated images.

The medical imaging apparatus 210 may be one of: a computed tomography (CT) scanner, a magnetic resonance imaging (MRI) scanner, a 3D ultrasound and the like. In some embodiments of the present technology, the medical imaging apparatus 210 may be a plurality of medical imaging apparatuses, such as one or more of a computational tomography (CT) scanner, a magnetic resonance imaging (MRI) scanner, a 3D ultrasound, and the like.

The medical imaging apparatus 210 may be configured with specific parameters for acquiring the plurality of images.

As a non-limiting example, in an embodiment where the medical imaging apparatus 210 is implemented as a CT scanner, a CT protocol comprising pre-operative retrospectively gated multidetector CT (MDCT—64-row multi-slice CT scanner) with variable dose radiation to capture the R-R interval may be used.

As another non-limiting example, in an embodiment where the medical imaging apparatus 210 is implemented as an MRI scanner, an MR protocol may be used and the MR protocol may comprise steady state T2 weighted fast field echo (TE=2.6 ms, TR=5.2 ms, flip angle 110 degree, fat suppression (SPIR), echo time 50 ms, maximum 25 heart phases 2, matrix 256×256, acquisition voxel MPS 1.56/1.56/3.00 mm and reconstruction voxel MPS 0.78/0.78/1.5).

The medical imaging apparatus 210 includes or is connected to a workstation computer 215.
Workstation Computer The workstation computer 215 is configured to receive and process the plurality of images from the medical imaging apparatus 210. The workstation computer 215 may receive images in raw format and perform a tomographic reconstruction using known algorithms and software. The implementation of the workstation computer 215 is known in the art. The workstation computer 215 may be implemented as the electronic device 100 or comprise components thereof, such as the processor 110, the graphics processing unit (GPU) 111, the solid-state drive 120, the random-access memory 130, the display interface 140, and the input/output interface 150.

In one embodiment, the workstation computer 215 may be integrated into the medical imaging apparatus 210.

In one embodiment, the workstation computer 215 is configured according to the Digital Imaging and Communications in Medicine (DICOM) standard for communication and management of medical imaging information and related data.

In one embodiment, the workstation computer 215 may store the images in a database (not depicted).

The workstation computer 215 is connected to a server 230 over the communications network 220 via a communication link (not numbered).
Server Generally speaking, the server 230 is configured to: (i) receive and process the plurality of images into a multiphase stack; (ii) generate 3D geometrical models of a lumen and an outer wall of a blood vessel from the multiphase stack; (iii) smooth and mesh the 3D geometrical models to obtain meshes of the lumen and the outer wall; (iv) calculate a thickness parameter based on the meshes of the lumen and the outer wall; (v) generate a computational flow dynamic (CFD) simulation using the mesh of the lumen to calculate a wall shear stress parameter or, alternatively, calculate a wall shear stress parameter from 4D-flow MRI data for a given patient; (vi) track and map the mesh of the outer wall to calculate a wall strain parameter; and (vii) determine a regional rupture potential parameter based on the thickness parameter, the wall strain parameter, and the wall shear stress parameter.

How the server 230 is configured to do so will be explained in more detail herein below.

The server 230 can be implemented as a conventional computer server and may comprise some or all of the components of the electronic device 100 depicted in FIG. 1. In an example of an embodiment of the present technology, the server 230 can be implemented as a Dell™ PowerEdge™ Server running the Microsoft™ Windows Server™ operating system. Needless to say, the server 230 can be implemented in any other suitable hardware and/or software and/or firmware or a combination thereof. In the depicted non-limiting embodiment of present technology, the server 230 is a single server. In alternative non-limiting embodiments of the present technology, the functionality of the server 230 may be distributed and may be implemented via multiple servers (not depicted).

Figure 3:
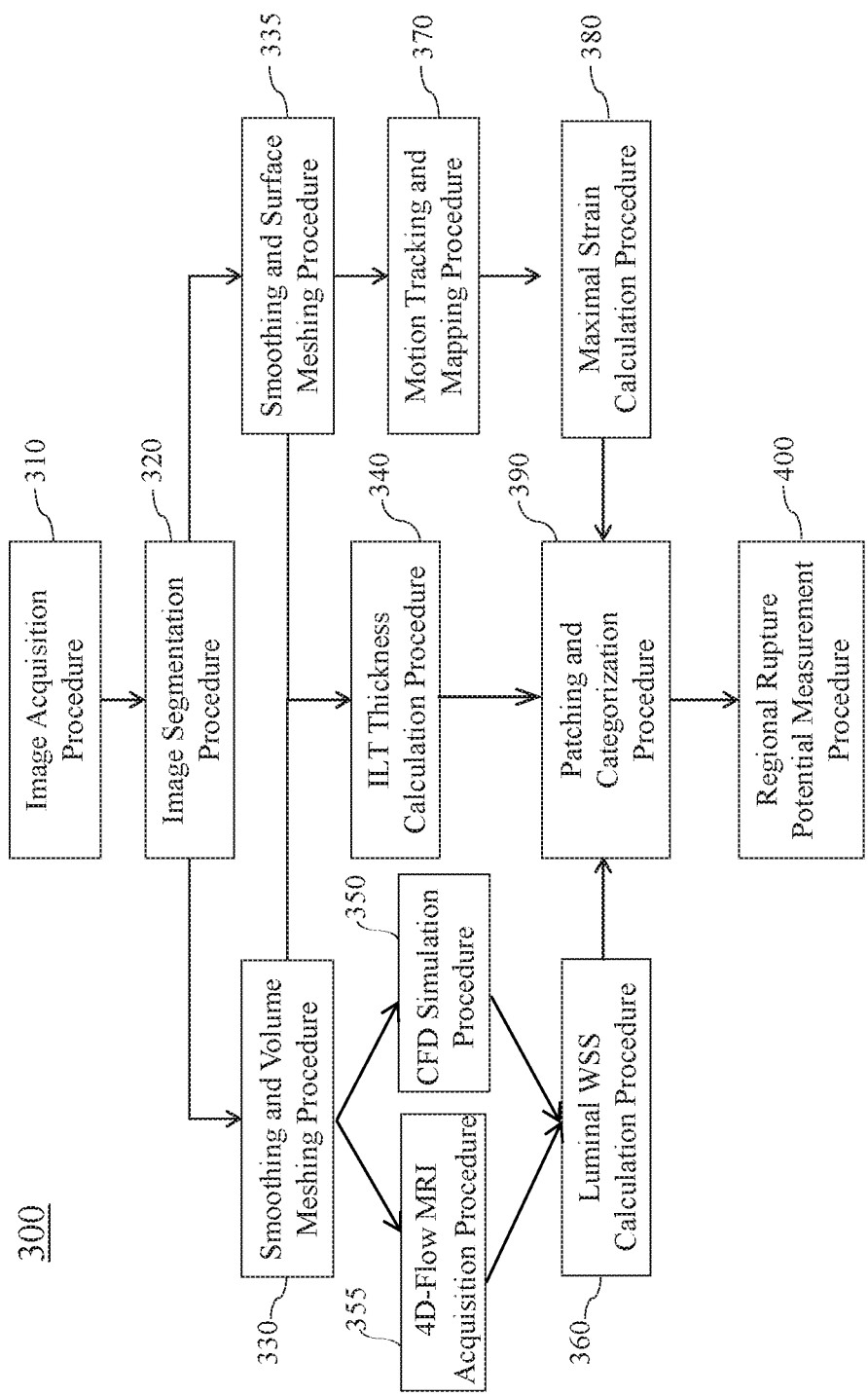
FIG. 3 depicts a schematic diagram of a regional rupture potential determination procedure, the regional rupture potential determination procedure being executed within the system of FIG. 2 in accordance with non-limiting embodiments of the present technology.

The implementation of the server 230 is well known to the person skilled in the art of the present technology. However, briefly speaking, the server 230 comprises a communication interface (not depicted) structured and configured to communicate with various entities (such as the workstation computer 215, for example and other devices potentially coupled to the network) via the communications network 220. The server 230 further comprises at least one computer processor (e.g., a processor 110 of the electronic device 100) operationally connected with the communication interface and structured and configured to execute various processes to be described herein.
Communication Network In some embodiments of the present technology, the communications network 220 is the Internet. In alternative non-limiting embodiments, the communication network 240 can be implemented as any suitable local area network (LAN), wide area network (WAN), a private communication network or the like. It should be expressly understood that implementations for the communication network 250 are for illustration purposes only. How a communication link 225 (not separately numbered) between the workstation computer 215 and/or the server 230 and/or another electronic device (not depicted) and the communications network 220 is implemented will depend inter alia on how each of the medical imaging apparatus 210, the workstation computer 215, and the server 230 is implemented.
Regional Rupture Potential Determination Procedure Now turning to FIG. 3, there is a depicted a schematic diagram of a regional rupture potential (RRP) determination procedure 300 in accordance with non-limiting embodiments of the present technology.

Figure 2:
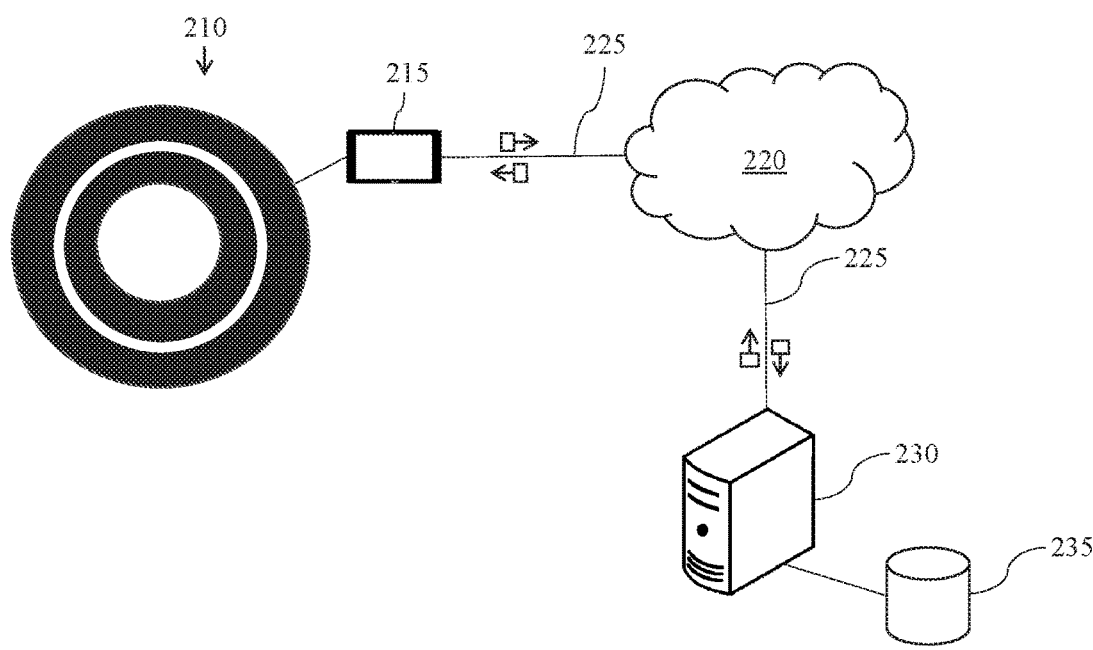
FIG. 2 depicts a schematic diagram of a system in accordance with non-limiting embodiments of the present technology.

The RRP determination procedure 300 is executed within the system of FIG. 2. In one embodiment, the RRP determination procedure 300 may be executed by the server 230. It is contemplated that some procedures of the RRP determination procedure 300 may be executed in parallel by the server 230 or by electronic devices (such as the workstation computer 215).

The RRP determination procedure 300 comprises inter alia an image acquisition procedure 310, an image segmentation procedure 320, a smoothing and volume meshing procedure 330, a smoothing and surface meshing procedure 335, an ILT thickness calculation procedure 340, a CFD simulation procedure 350 or 4D-flow MRI acquisition procedure 355, a luminal WSS calculation procedure 360, a motion tracking and mapping procedure 370, a patching and categorization procedure 390, and an RRP calculation procedure 400.

Image Acquisition

The image acquisition procedure 310 is executed by the medical imaging apparatus 210 and the workstation computer 215.

During the image acquisition procedure 310, a plurality of images of a blood vessel, such as an aorta of a given patient, are received. The plurality of images may be received from the workstation computer 215 or directly from the medical imaging apparatus 210.

In one embodiment where the medical imaging apparatus 210 is a CT scanner, the CT protocol for CT image acquisition can comprise pre-operative retrospectively gated MDCT (64-row multi-slice CT scanner) with variable dose radiation to capture the R-R interval. In one embodiment where the medical imaging apparatus 210 is a MRI scanner, the MR protocol can comprise steady state T2 weighted fast field echo (TE=2.6 ms, TR=5.2 ms, flip angle 110 degree, fat suppression (SPIR), echo time 50 ms, maximum 25 heart phases 2, matrix 256×256, acquisition voxel MPS 1.56/1.56/3.00 mm and reconstruction voxel MPS 0.78/0.78/1.5), or similar cine acquisition of the portion of aorta under study, axial slices.

The image acquisition procedure 310 organizes the plurality of images in a multiphase stack. In one embodiment, the plurality of images is organized in phases according to a Digital Imaging and Communications in Medicine (DICOM) stack, the implementation of which is known in the art.

In one embodiment, each phase of the multiphase stack may correspond to a time instance in the cardiac cycle of the given patient.

The image acquisition procedure 310 outputs the multiphase stack.

Image Segmentation

The image segmentation procedure 320 receives as an input images corresponding to one phase of the multiphase stack.

The image segmentation procedure 320 uses segmentation techniques, which are known to the person skilled in the art, to identify pixels or voxels belonging to an object such as the blood vessel and/or locating those that form the boundary of the blood vessel to generate a 3D geometrical model of at least a portion of the blood vessel. The image segmentation procedure 320 may segment the stack based on one or more of pixel intensity, texture, and other attributes, using deformable models and techniques such as, but not limited to, low-level segmentation (thresholding, region growing, etc.), model based segmentation (multispectral, feature maps, dynamic programming, counter following), statistical techniques, fuzzy techniques as well as other techniques known in the art.

The image segmentation procedures 320 generates, based on the multiphase stack: (i) a 3D geometrical model of the lumen of the blood vessel; and (ii) a 3D geometrical model of the outer wall of the blood vessel. In one embodiment, the image segmentation procedure 320 may generate, based on a first phase of the multiphase stack, corresponding to a given time in the cardiac cycle identified as phase 0, a 3D geometrical model of the lumen, and a 3D geometrical model of the outer wall.

With brief reference to FIG. 4A, a 3D geometrical model of the lumen and the outer wall 420 of an infrarenal abdominal aortic aneurysm is depicted in accordance with non-limiting embodiments of the present technology.

Turning back to FIG. 3, the image segmentation procedure 320 outputs the 3D geometrical model of the lumen and the 3D geometrical model of the outer wall.

Smoothing and Volume Meshing

The smoothing and volume meshing procedure 330 receives as input the 3D geometrical model of the lumen.

Generally speaking, the smoothing and volume meshing procedure 330 filters or denoises the 3D geometrical model of the lumen and creates a discrete representation thereof comprising vertices, edges and faces.

The smoothing and volume meshing procedure 330 smooths the 3D geometrical model of the lumen, and generates a volume mesh of the 3D geometrical model of the lumen.

In one embodiment, the smoothing and meshing volume procedure 330 generates the volume mesh of the 3D geometrical model of the lumen with a top-down approach by means of the octree method: a first coarse mesh is defined to enclose the geometry and is then spatially subdivided into smaller elements whose nodes are adapted to the geometry surface by means of swapping and smoothing to reach a desired mesh quality. Prismatic boundary layers (finer mesh) are included at the geometry wall in order to improve results accuracy at this region of interest. As a non-limiting example, the volume mesh of the lumen may have approximately 4 million tetrahedral elements.

The smoothing and volume meshing procedure 330 outputs the volume mesh of the 3D geometrical model of the lumen.

Smoothing and Surface Meshing

The smoothing and surface meshing procedure 335 receives as an input the 3D geometrical model of the outer wall. The smoothing and surface meshing procedure 335 filters or denoises the 3D geometrical model of the outer wall and creates a discrete representation thereof comprising vertices, edges and faces.

The smoothing and surface meshing procedure 335 smooths the 3D geometrical model of the outer wall, and generates a surface mesh of the 3D geometrical model of the outer wall. In one embodiment, the surface mesh of the 3D geometrical model of the outer wall is in the form of discretized geometry of small triangular elements or shells.

In one embodiment, the smoothing and surface meshing procedure 335 uses a Taubin filter for smoothing and/or a quadric edge collapse decimation to reduce a number of shells. As a non-limiting example, the surface mesh of the outer wall may have approximately 4,000 triangular shell elements.

In one embodiment, the resolution of the surface mesh of the 3D geometrical model of the outer wall is at least as big as the pixel size. In one embodiment, the surface mesh of the outer wall is a deformable mesh.

The smoothing and surface meshing procedure 335 outputs the surface mesh of the 3D geometrical model of the outer wall.

Thickness Calculation

The thickness calculation procedure 340 receives as input the surface mesh of the outer wall and the volume mesh of the lumen.

The thickness calculation procedure 340 determines a thickness parameter based on: the surface mesh of the outer wall and the volume mesh of the lumen.

Generally speaking, the thickness parameter includes intraluminal thrombus (ILT) thickness measurements. The thickness calculation procedure 340 determines the ILT thickness based on the distance between the outer wall surface mesh and a lumen surface mesh. The thickness calculation procedure 340 obtains the lumen surface mesh based on the volume mesh of the lumen. The thickness parameter is a spatial distribution of ILT thickness measurements.

In one embodiment, if there is enough resolution to discriminate between the interface between the ILT surface and the interior surface of the wall, the thickness calculation procedure 340 determines a thickness parameter based on the distance between the interior surface of the wall and the exterior surface of the wall. In one embodiment, the thickness calculation procedure 340 may determine ILT thickness only when there is presence of an ILT. Thus, in one embodiment, the thickness parameter may include the ILT thickness and/or the wall thickness.

In one embodiment the surface mesh of the lumen is obtained from the volume mesh of the lumen.

It should be noted that a number of values of ILT thickness in the thickness parameter is not limited and depends on how the surface mesh of the outer wall and the surface mesh of the lumen have been generated, i.e. the ILT thickness may be measured between each element of the surface mesh of the outer wall and the surface mesh of the lumen, or between a subset of elements of the surface mesh of the outer wall and the surface mesh of the lumen.

Figure 6A:
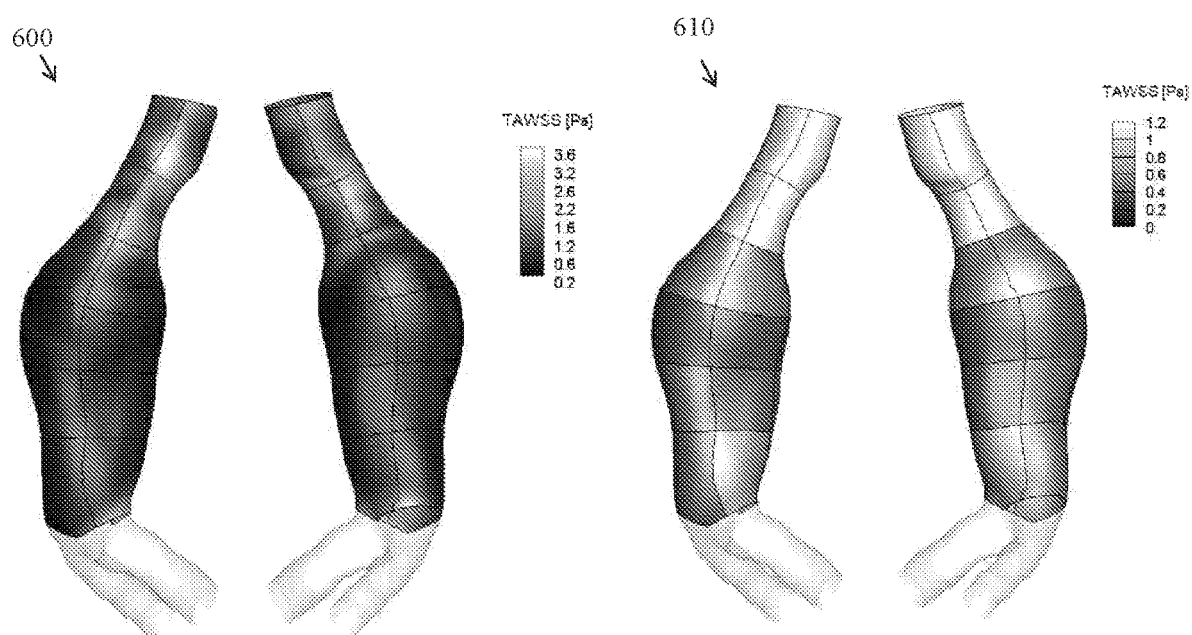
FIG. 6A illustrates a distribution of TAWSS and a region-averaged distribution of TAWSS on a luminal surface in accordance with non-limiting embodiments of the present technology.
Figure 6B:
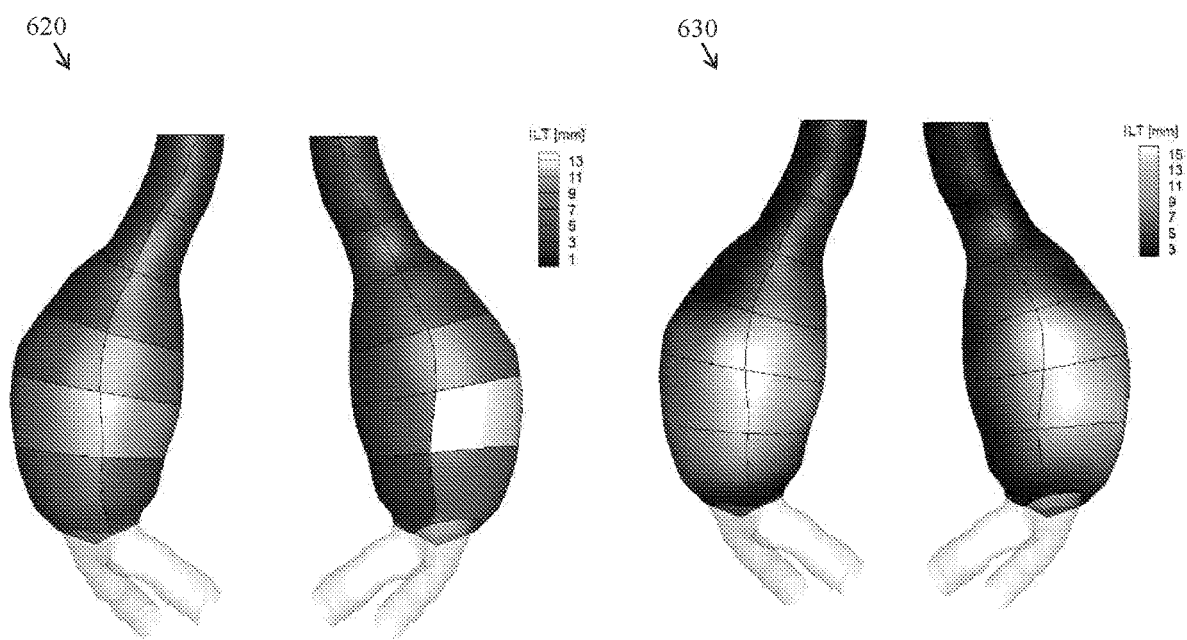
FIG. 6B illustrates a distribution of ILT thickness and a region-averaged distribution of ILT thickness on an outer wall surface in accordance with non-limiting embodiments of the present technology.

With brief reference to FIG. 6B, there is illustrated a distribution of ILT thickness measurements 630 and a region-averaged distribution of ILT thickness measurement 620 in millimeters (mm) on an outer wall surface in accordance with non-limiting embodiments of the present technology.

Turning back to FIG. 3, the thickness calculation procedure 340 outputs the thickness parameter.

Motion Tracking and Mapping

The motion tracking and mapping procedure 370 receives as inputs the surface mesh of the 3D geometrical model of the outer wall and the multiphase stack of images for all phases.

In one embodiment, the motion tracking and mapping procedure 370 is executed by the MATLAB (The MathWorks, Inc., Natick, Massachusetts, United States of America)-based software Virtual Touch Aortic Aneurysm (ViTAA™) of which embodiments are described in International Patent Publication WO 2018/068153 A1.

The motion tracking and mapping procedure 370 uploads the surface mesh of the 3D geometrical model of the outer wall created for the first phase onto the multiphase stack.

The motion tracking and mapping procedure 370 maps each voxel position of the surface mesh for the first phase to all the subsequent phases using an optical flow (OF) algorithm. The position of all the voxels at the different phases is mapped back to the surface mesh for the first phase, where each node position of the geometry at the first phase is associated with node positions corresponding to all the subsequent phases. Thus, nodal displacement throughout the cardiac cycle, i.e. different phases, may be determined.

In one embodiment, the motion tracking and mapping procedure 370 follows the displacement of an object between images taken at subsequent time steps by detecting the grayscale feature corresponding to the object and computing its velocity.

As a non-limiting example, for CT images, the nodes corresponding to the first phase will have corresponding node positions for all the subsequent phases.

From the map of the displaced nodes, the motion tracking and mapping procedure 370 generates deformed meshes at all phases. The position of all the voxels at the different phases is mapped back to the mesh for the first phase so that each node position of the geometry at the first phase is associated with node positions corresponding to all the subsequent phases.

That is, the mesh generated from 320 and 335 is used to generate deformed meshes at all phases by updating the coordinate location for each nodal point of the mesh.

The motion tracking and mapping procedure 370 outputs the local deformation at each phase of the surface mesh.

Maximum Strain Calculation

The maximal strain calculation procedure 380 receives as input the local deformation at each phase of the surface mesh and the surface mesh for the first phase.

The maximal strain calculation procedure 380 uses continuum mechanics techniques to compute in vivo strains based on the local kinematics at each phase of the surface mesh.

For example, given three nodes composing a triangular shell element on the surface for Phase 0, the rectangular coordinate system is introduced with the center at node 1 and three vectors, A1 pointing from node 1 to node 2, A2 from node 1 to node 3, and an out of plane unit vector A3 perpendicular to the other two are defined. For each of the subsequent phases the referential vectors A1, A2 and A3 are mapped into the corresponding spatial vectors a1, a2 and a3 respectively. The spatial coordinates are defined for a new coordinate system with the center at the new position of node 1, and the mapping is carried out with the help of the deformation gradient $[a_k]^i = F_I^i [A_k]^I$ with k=1, 2, 3, $[A_k]^I$ the I-th component of $A_k$, $[a_k]^i$ the i-th component of $a_k$ and $F_I^i$ the iI-th component of the deformation gradient tensor F. Since the in-plane referential and spatial vector components are known from the tracking, and there is an additional constrain due to the incompressibility of the tissue, all the components of the deformation gradient F can be determined by solving a system of equations. The person skilled in the art will appreciate that while the present example refers to a triangular shell element, shell elements having a shape other than a triangular shape may be used.

In one embodiment, the maximal strain calculation procedure 380 takes the deformation gradient F and computes the non linear Green-Lagrange strain tensor $E=\frac{1}{2}(C-I)$, which is then diagonalized to obtain principal strain values. The maximal strain values are computed as the maximum of the three principal strain values at every phase along the principal strain direction (the wall strain parameter).

In one embodiment, the maximal strain calculation procedure 380 first computes a deformation gradient, from which it computes a Cauchy-Green deformation tensor, and then computes the Green-Lagrange strain. The maximal strain calculation procedure 380 then computes the principal strains as eigenvalues of the Green-Lagrange strain to generate the wall strain parameter. The wall strain parameter is a distribution of maximal principal strains measurements.

It should be noted that a number of values of maximal principal strain in the wall strain parameter is not limited and depends on the number of displaced nodes that have been tracked on the surface mesh.

Figure 6C:
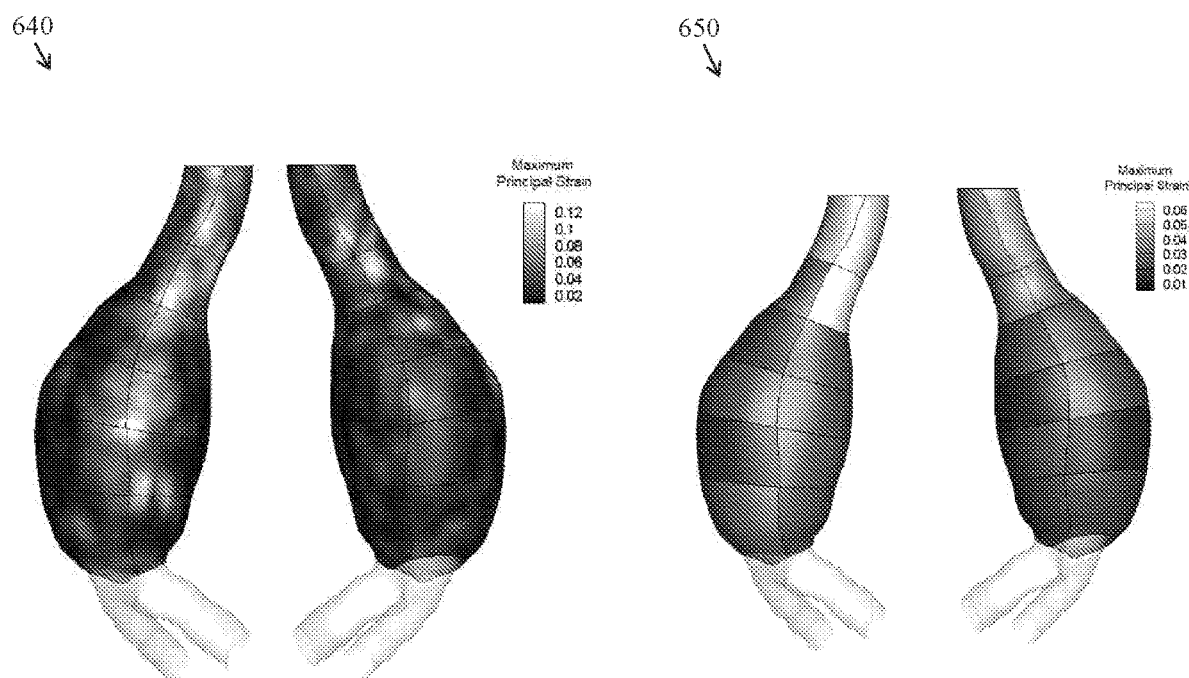
FIG. 6C illustrates a distribution of maximum principal strain and a region-averaged distribution of maximum principal strain on an outer wall surface in accordance with non-limiting embodiments of the present technology.

With brief reference to FIG. 6C, there is depicted a distribution of maximum principal strain on the outer wall surface 640 and a region-averaged distribution of maximum principal strain on the outer wall surface 650 in accordance with non-limiting embodiments of the present technology.

Turning back to FIG. 3, the maximal strain calculation procedure 380 outputs the wall strain parameter, the wall strain parameter being representative of relative displacement of regions of the outer wall.

Computational Fluid Dynamics (CFD) Simulation

The computational fluid dynamic (CFD) simulation procedure 350 receives as input the volume mesh of the 3D geometrical model of the lumen.

Generally speaking, the CFD simulation procedure 350 simulates blood flow in the arterial geometry by employing a finite volume method for the numerical implementation of the Navier-Stokes equations describing fluid flow. The CFD simulation procedure 350 uses finite volume method to solve the discretized form of the Navier-Stokes equations over all the finite volume elements in the domain. The CFD simulation procedure 350 applies an iterative approach to simulate blood flow to obtain a converged numerical solution due to the governing equations being non-linear and coupled. It should be noted that in alternative embodiments of the present technology, finite element or finite difference methods could be used instead of finite volume methods to obtain the same CFD parameters.

The CFD simulation procedure 350 uses a second order implicit transient formulation and predefined CFD parameters including inter alia boundary conditions, viscosity, density, and time step.

Generally, a computational domain or discretized geometry is defined.

The CFD simulation procedure 350 applies boundary conditions at the domain inlet, outlets and wall in order to solve the Navier-Stokes equations describing the fluid dynamics or blood flow. It should be noted that realistic boundary conditions are important for reliability: using unrealistic boundary conditions for the aorta would allow a solution to be reached, but the results would be clearly unreliable, because non-representative of a realistic fluid dynamics. In one embodiment, boundary conditions are based on an atlas of velocity boundary conditions obtained from experimental MR measures and adapted to each individual geometry.

In one embodiment, the CFD simulation procedure 350 defines a velocity inlet by applying velocity information at the inlet surface of the computational domain. A constant velocity value will produce a steady-state simulation while the application of a velocity profile in time it is needed for a time-dependent simulation (transient time or unsteady simulation). In one embodiment, where the boundary conditions at the outlet defined as outflow boundary conditions, the flow rate at the outlets is expressed as a percentage of the inlet flow rate, which may be, as a non-limiting example, 50% in each iliac artery.

The CFD simulation procedure 350 uses a rheological model for the blood i.e. Newtonian or non-Newtonian behavior, by using specified viscosity, which is constant for a Newtonian fluid, and shear rate dependent for non-Newtonian fluids, and a density.

In one embodiment, the rheological model assumes the blood to be an isotropic, incompressible, Newtonian fluid with assigned constant density (e.g. 1060 kg/m3) and dynamic viscosity (e.g. 0.00319 Pa·s). The arterial wall is assumed to be rigid and a no-slip condition is applied at fluid interface.

Generally speaking, the assumption of blood behavior as a Newtonian fluid (i.e. shear stress linearly proportional to shear rate by mean of constant viscosity) is well accepted for larger cardiovascular districts characterized by elevated shear rates. At lower shear rates, however, the blood behavior varies from that of a Newtonian fluid, assuming shear-thinning characteristics with viscosity that changes according to shear rate. The non-Newtonian behavior of blood can be simulated by using a different rheological model that accounts for the shear-rate dependency of the blood viscosity (e.g. Ballyk model, Carreau-Yasuda model).

In one embodiment, the movement of the arterial wall can be incorporated by means of fluid-structure interaction (FSI) simulation, where the effects of wall dynamics are considered to affect the fluid, and vice versa. The FSI simulation requires the assumption of wall material properties, described through a constitutive model. Different constitutive models are available, but not always accurate in capturing the inter and intra patient heterogeneity characterizing the aortic wall, especially in the presence of pathological aneurysms. Moreover, a simulation including a moving arterial wall requires the definition of constraints to reproduce the effects of surrounding organs, with unknown material properties, and limit the wall movements. Thus, the assumptions required to simulate a moving arterial wall are likely to introduce inaccuracies in the results of the CFD simulation procedure 350.

In one embodiments, the CFD simulation can use the position of the nodal mesh of the wall as obtained from the wall strain algorithm, to define a moving boundaries CFD simulation where the effects of the wall dynamics are incorporated by imposing the movement of the wall in the simulation.

The CFD simulation procedure 350 uses, for a transient-time or unsteady simulation, a time step, the time step defining the temporal discretization of the equations to be solved.

It should be noted that the accuracy of results of the CFD simulation procedure 350 is affected by the spatial and temporal discretization, i.e. the mesh elements size and time step size. A coarser mesh and a larger time step size would still allow the simulation to run, although leading instabilities and, eventually, less accurate results. It should be noted that increased accuracy is reached by using a volume mesh of the lumen that includes prismatic boundary layers in the near wall region.

In one embodiment, a mesh sensitivity analysis may be conducted to identify the appropriate mesh refinement to obtain optimal results during the CFD simulation procedure 350. The appropriate mesh refinements are applied during the smoothing and volume meshing procedure 330.

The CFD simulation procedure 350 outputs a blood flow parameter, the flow parameter including a respective set of flow values such as velocity and pressure at each of the nodes of the lumen mesh for a cardiac cycle.

With brief reference to FIG. 5, there is depicted values of a blood flow parameter 500 predicted after a CFD simulation procedure on a longitudinal cross section of an AAA at different times of the cardiac cycle in accordance with non-limiting embodiments of the present technology.

The blood flow parameter 500 is in the form of velocity contours expressed in meters per second (m/s). The blood flow parameter 500 comprises a first set of velocity values 520 during systolic acceleration, a second set of velocity values 540 during systolic peak, a third set of velocity values 560 during systolic deceleration, and fourth set of velocity values 580 during diastole.

In one embodiment, the CFD simulation procedure 350 is replaced by computing the blood flow parameters by using 4D-flow MRI acquisition procedure 355. The 4D-flow MRI acquisition procedure 355 receives as input the volume mesh of the 3D geometrical model of the lumen. The 4D-flow MRI acquisition procedure 355 uses the volume mesh of the 3D geometrical model of the lumen to identify volume portions in which the velocity field is measured.

In one embodiment, the 4D-flow MRI acquisition procedure 355 comprises ECG-triggered and breath-triggered data acquisition. In one embodiment, the data may be acquired by the medical imaging apparatus 210 when it is implemented as a MRI, or by another MRI (not depicted).

As a non-limiting example, the 4D-flow MRI acquisition procedure 355 may use the following acquisition parameters: repetition time=4.8±0.1 ms, echo time=2.4±0.1 ms, isotropic pixel in-plane spacing=2.2±0.2 [1.7–2.9] mm, slice thickness=2.7±0.3 [2.2-3.5 mm; 2 k-space segments per cardiac time frame, temporal resolution=38.8±1.2 [36.0–41.6] ms, and receiver bandwidth=445-460 Hz/pixel.

Several magnitude pictures may be taken through different reconstruction processes, such as, but not limited to, parallel imaging to perform reconstruction. Pictures in all space axes may then be calculated. Phase-offset errors may also be corrected during preprocessing. Analysis may be performed and during the analysis phase the datasets will be checked for quality first for subsequent visualization and quantitative analysis. The blood flow parameter may then be determined by obtaining the velocity field in the volume corresponding to the volume mesh of the 3D geometrical model of the lumen.

The 4D-flow MRI acquisition procedure 355 outputs the blood flow parameter, the blood flow parameter including a respective set of flow values in the lumen for a cardiac cycle.

Luminal Wall Shear Stress (WSS) Calculation

Turning back to FIG. 3, the luminal WSS calculation procedure 360 receives as an input a blood flow parameter calculated during the CFD simulation procedure 350. In one embodiment, the luminal WSS calculation procedure 360 receives as an input the blood flow parameter calculated during the 4D-flow MRI acquisition procedure 355.

Generally speaking, the luminal WSS calculation procedure 360 quantifies wall shear stress (WSS) disturbances based on the blood flow parameter to output a wall shear stress parameter. In one embodiment, the WSS is defined as: $\tau = \mu \gamma$, where $\mu$ is the blood dynamic viscosity and $\gamma$ is the shear rate defined as $$\frac{\partial v_x}{\partial y}$$

with v being the blood flow velocity along the boundary at an instant of the cardiac cycle.

In one embodiment, the luminal WSS calculation procedure 360 derives all-shear stress based hemodynamic wall descriptors (HWD) from the set of flow values. The HWD incorporate temporal variation of the magnitude and direction of the WSS vector.

The luminal WSS calculation procedure 360 calculates a wall shear stress parameter for each node at the lumen surface based on at least one HWD.

In one embodiment, the luminal WSS calculation procedure 360 determines a first HWD or time averaged wall-shear stress (TAWSS) by using equation (1):

$$TAWSS = \frac{1}{T} \int_0^T |WSS(s, t)| dt \quad (1)$$

where T is the time interval during which the values of a WSS vector are measured.

Generally, low values of the TAWSS (lower than 0.4 N/m2) are known to stimulate a proatherogenic endothelial phenotype and are indicative of intima/media complex thickening. Moderate values of the TAWSS (greater than 1.5 N/m2) TAWSS values induce quiescence and an atheroprotective gene expression profile. Higher values of the TAWSS (greater than 10÷15 N/m2, relevant from 25÷45 N/m2) can lead to endothelial trauma and hemolysis.

With brief reference to FIG. 5A, there is depicted a distribution of TAWSS 600 and a region-averaged distribution of TAWSS 610 on a luminal surface in pascals (Pa) in accordance with non-limiting embodiments of the present technology.

Turning back to FIG. 3, in one embodiment, the luminal WSS calculation procedure 360 determines a second HWD or oscillatory shear index (OSI) by using equation (2):

$$OSI = 0.5 \left[ 1 - \left( \frac{\left| \int_0^T WSS(s, t) dt \right|}{\int_0^T |WSS(s, t)| dt} \right) \right] \quad (2)$$

OSI is used to identify regions on the vessel wall subjected to highly oscillating WSS directions during the cardiac cycle. Low OSI values occur at sites where flow disruption is minimal, whereas high OSI values (with a maximum of 0.5) highlight sites where the instantaneous WSS deviates from the main flow direction in a large fraction of the cardiac cycle, inducing perturbed endothelial alignment.

In one embodiment, the luminal WSS calculation procedure 360 determines a third HWD or relative residence time (RRT) by using equation (3):

$$RRT = \frac{1}{(1 - 2 \cdot OSI) \cdot TAWSS} \quad (3)$$

It should be noted that RRT is inversely proportional to the magnitude of the time-averaged WSS vector (i.e., the term in the numerator of the OSI formula). The residence time of particles near the wall is proportional to a combination of OSI and TAWSS. A high RRT is indicative of a low and oscillatory shear stress.

The luminal WSS calculation procedure 360 determines the wall shear stress parameter based on the TAWSS. It is contemplated that in alternative embodiments of the present technology, the luminal WSS calculation procedure 360 may determine the wall shear stress parameter further based on at least one of: the TAWSS, the OSI, and the RRT.

The wall shear stress parameter is indicative of flow disturbances in the lumen or components of stress coplanar with regions of the lumen cross section.

Patching and Categorization

The patching and categorization procedure 390 receives as inputs the thickness parameter, the wall strain parameter and the wall shear stress parameter.

The patching and categorization procedure 390 defines a plurality of patches on the vessel geometries comprising the outer wall and the lumen, perpendicularly to the lumen centerline, and determines a patch-averaged distribution for each of the thickness parameter, the wall strain parameter and the wall shear stress parameter.

As a non-limiting example, the patching and categorization procedure 390 may define twenty-four patches on the vessel geometries of the outer wall and the lumen, and compute for each of the twenty-four patches, values for the wall thickness, the wall strain, and the wall shear stress. As a non-limiting example, if a given patch corresponds to forty elements of the mesh where forty values of wall shear stress are present in the wall shear stress parameter, the patching and categorization procedure 390 may calculate an average of the forty values of wall shear stress for the given patch.

In one embodiment, the patching and categorization procedure 390 receives population-based values for each of the thickness parameter, the wall strain parameter and the wall shear stress parameter.

In one embodiment, the patching and categorization procedure 390 determines distribution quartiles of the patch-averaged distribution of: the ILT thickness, the wall strain, and the TAWSS. In one embodiment, the distribution quartiles are determined for each patch-averaged distribution of the patient specific distribution and the population-based distribution.

In one embodiment, the patching and categorization procedure 390 classifies, for each patch, the ILT thickness, the wall strain and the TAWSS based on the determined distribution quartiles.

In one embodiment, the patching and categorization procedure 390 assigns a category from 1 to 4 to each value in the patch-averaged thickness parameter, the patch-averaged wall strain parameter, and the patch-averaged wall shear stress parameter.

As a non-limiting example, for the thickness parameter, the wall strain parameter, and the wall shear stress parameter depicted respectively from FIG. 6A to 6C, the patching and categorization procedure 390 obtains for each patch in the patch-averaged thickness parameter, the patch-averaged wall strain parameter, and the patch-averaged wall shear stress parameter, the values and the categories detailed in Table I:

TABLE I

| Patch | TAWSS | ILT | Maximal Principal Strain |
|---|---|---|---|
| LA1 | 3 | 1 | 4 |
| LP1 | 4 | 1 | 4 |
| RP1 | 4 | 1 | 4 |
| RA1 | 4 | 1 | 4 |
| LA2 | 3 | 1 | 3 |
| LP2 | 4 | 2 | 4 |
| RP2 | 4 | 2 | 4 |
| RA2 | 4 | 1 | 3 |
| LA3 | 2 | 2 | 1 |
| LP3 | 2 | 3 | 2 |
| RP3 | 3 | 2 | 2 |
| RA3 | 3 | 2 | 3 |
| LA4 | 1 | 3 | 3 |
| LP4 | 1 | 4 | 2 |
| RP4 | 1 | 3 | 1 |
| RA4 | 2 | 4 | 1 |
| LA5 | 2 | 4 | 1 |
| LP5 | 1 | 4 | 3 |
| RP5 | 1 | 3 | 2 |
| RA5 | 2 | 4 | 1 |
| LA6 | 1 | 3 | 3 |
| LP6 | 3 | 3 | 2 |
| RP6 | 3 | 2 | 2 |
| RA6 | 2 | 4 | 1 |

The patching and categorization procedure 390 outputs, for each patch, a respective category for the patch-averaged TAWSS, the patch-averaged thickness parameter, and the patch-averaged wall strain parameter.

Regional Rupture Potential (RRP) Calculation

The RRP calculation procedure 400 receives as inputs respective categories for the patch-averaged thickness parameter, the patch-averaged wall strain parameter and the patch-averaged wall shear stress parameter.

In another embodiment, the RRP calculation procedure 400 receives as inputs the thickness parameter, the wall strain parameter and the wall shear stress parameter and determines the RRP parameter. In a further embodiment, the RRP calculation procedure 400 receives the patch-averaged thickness parameter, the patch-averaged wall strain parameter and the patch-averaged wall shear stress parameter and determines the RRP parameter.

In one embodiment, the RRP calculation procedure 400 determines a regional rupture potential (RRP) parameter. The RRP parameter may be representative of a state of regional weakening and probabilities of rupture of a region or a set of regions of a blood vessel wall. The RRP parameter takes into account different factors to adverse remodeling and degeneration of a vessel wall, including but not limited to the aortic wall, and is indicative of a localized state of weakening of the blood vessel and consequent expansion and rupture potential.

In one embodiment, the RPP parameter corresponds to a weighted summation of the inputs. For example, the RRP calculation procedure 400 may determine the RRP parameter using equation (4):

$$RRP = \frac{[ILT_{category} + STRAIN_{category} + (5 - TAWSS_{category})] - 3}{9} \cdot 100 \quad (4)$$

where $ILT_{category}$, $STRAIN_{category}$, and $TAWSS_{category}$ are categories from 1 to 4 assigned respectively to the patch-averaged thickness parameter, the patch-averaged wall strain parameter, and the patch-averaged wall shear stress parameter.

In embodiments where no thrombus is present for a particular artery, the ILT thickness in the thickness parameter may have values of 0 everywhere, and the RRP calculation procedure 400 determines the RRP based on the wall shear stress parameter, and the wall strain parameter, as not all aneurysms present an ILT formation.

In one embodiment, the RRP calculation procedure 400 determines the RRP parameter for patient-specific distribution quartiles and for population-based distribution quartiles. In one embodiment, the RRP calculation procedure 400 weighs the contribution of patient-specific distribution quartiles and population-based distribution quartiles to obtain a final RRP parameter estimate. In one embodiment, the RRP calculation procedure 400 accesses a machine learning algorithm (MLA) having been trained to determine the RRP parameter based on clinical data and previously computed RRP parameters.

The RRP calculation procedure 400 outputs the RRP parameter, the RRP parameter including a rupture potential for each of the patches or regions defined during the patching and categorization procedure 390. In one embodiment, the RRP parameter may be in the form of a percentage varying from 0% (unlikely to rupture) to 100% (very likely to rupture) indicative of the expansion and rupture potential of each of the patches.

In one embodiment, the RRP calculation procedure 400 outputs the RRP parameter with a 3D geometrical model of the blood vessel on a display screen of an electronic device, such as the display interface 140 of the electronic device. In one embodiment, values of the RRP in the RRP parameter may be determined using a predetermined threshold.

Figure 7:
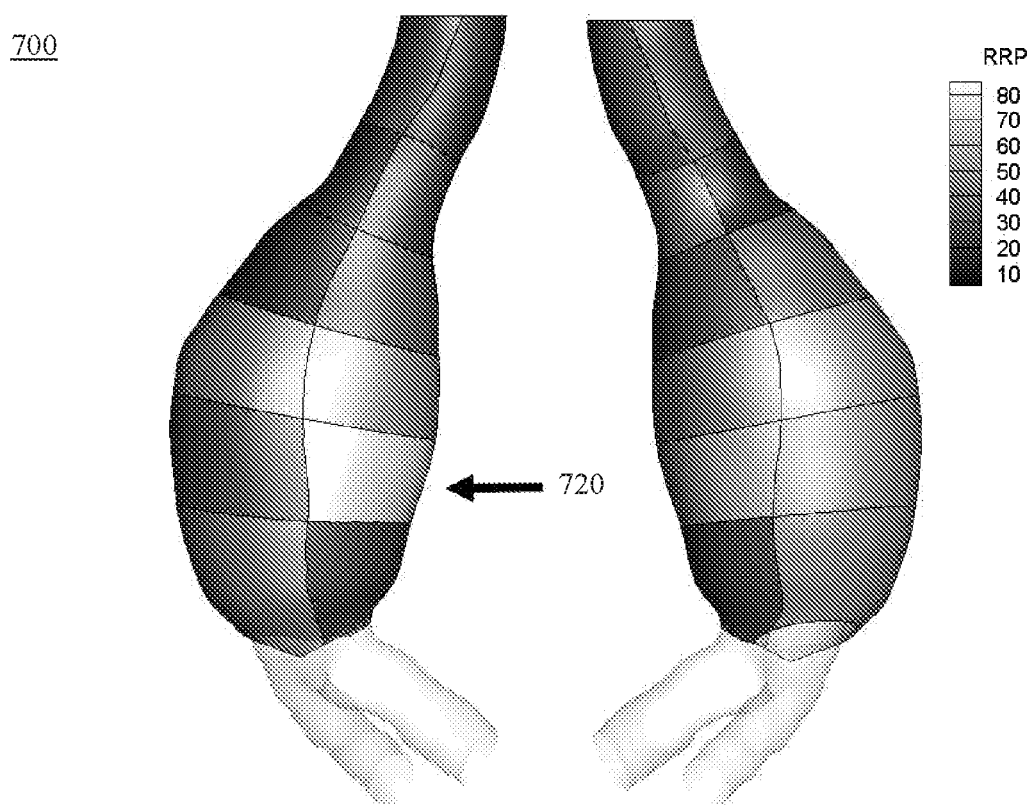
FIG. 7 illustrates a Regional Rupture Potential (RRP) computed on patches on an aortic wall surface with an estimated site of rupture in accordance with one non-limiting embodiment of the present technology.

With reference to FIG. 7, there is depicted a RRP parameter 700 which includes RRP values computed on patches on an aortic wall surface with an estimated site of rupture 720 located at patch LP5 in accordance with non-limiting embodiments of the present technology.

Method Description

Figure 8:
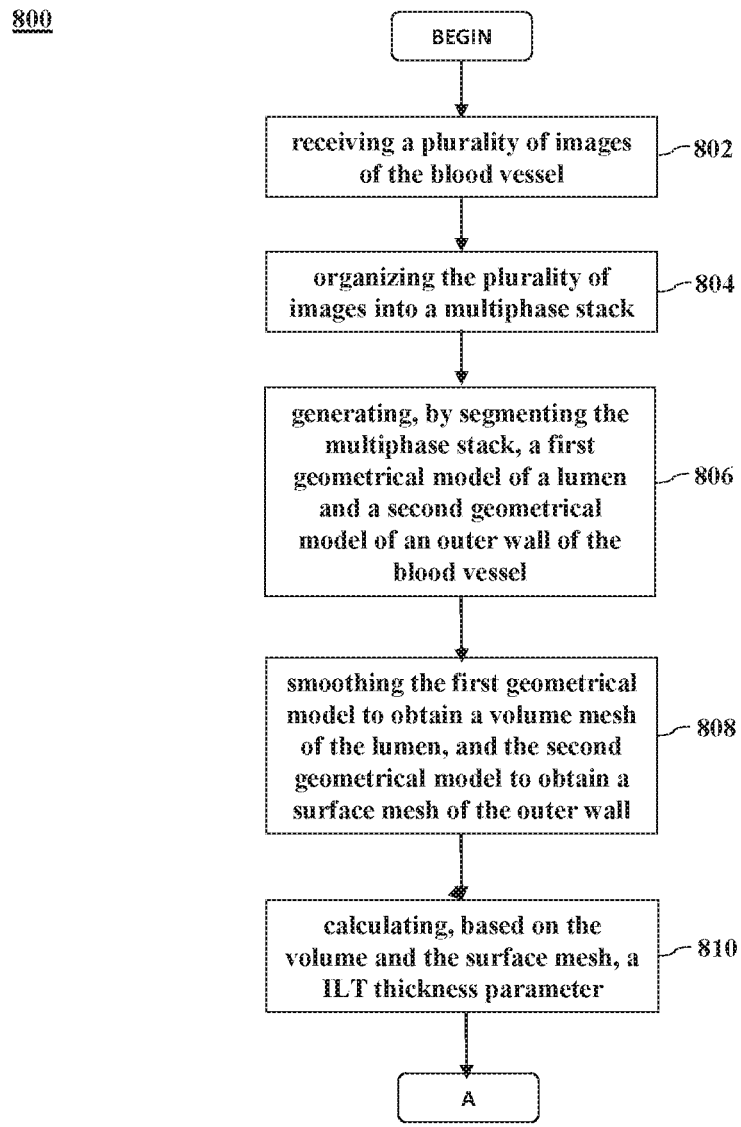
FIG. 8 and FIG. 9 depict a flow chart of a method of determining a regional rupture potential in accordance with non-limiting embodiments of the present technology.
Figure 9:
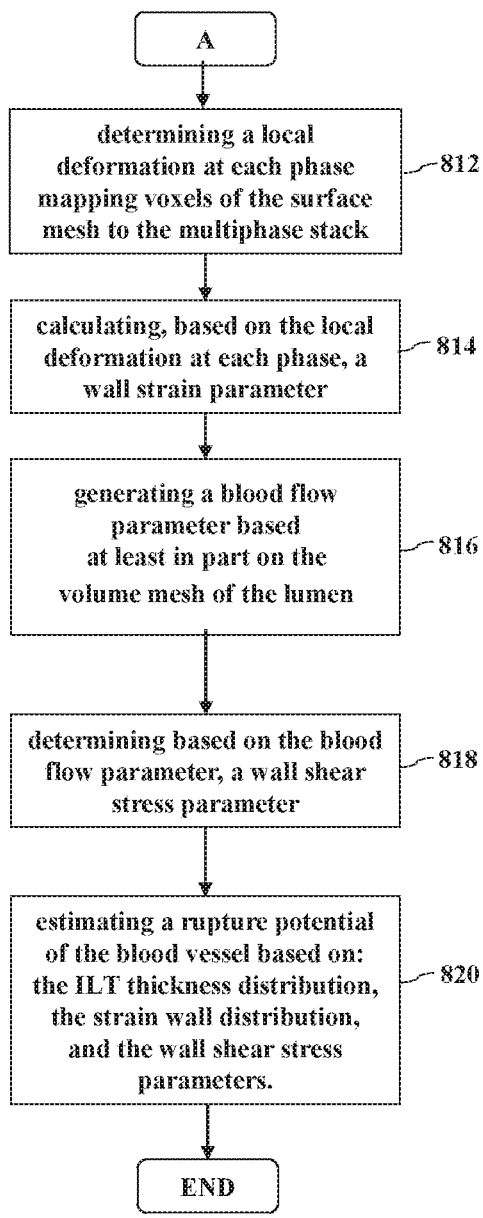

FIG. 8 depicts a flowchart of a method 800 of estimating a regional rupture potential of a blood vessel of a given patient in accordance non-limiting embodiments of the present technology.

The method 800 is executed by a computer machine. For example, the method 800 may be executed by the server 230. In one embodiment, the server 230 comprises a processor 110 and a non-transitory computer readable storage medium such as the solid-state drive 120 and/or the random-access memory 130 storing computer-readable instructions. The processor 110, upon executing the computer-readable instructions, is configured to execute the method 800.

It should be noted that the method 800 may be executed by more than one electronic device.

The method 800 begins at step 802.

STEP 802: Receiving a Plurality of Images of the Blood Vessel

At step 802, the server 230 receives, from the workstation computer 215 or the medical imaging apparatus 210, a plurality of images of the blood vessel of a given subject.

In one embodiment, the workstation computer 215 receives the plurality of images from the medical imaging apparatus 210.

The method 800 advances to step 804.

STEP 804: Organizing the Plurality of Images into a Multiphase Stack

At step 804, the server 230 organizes the plurality of images into a multiphase stack. In one embodiment, the workstation computer 215 may organize the plurality of images into the multiphase stack and transmit the multiphase stack to the server 230. A given phase of the multiphase stack is representative of the blood vessel at a given time in a cardiac cycle.

The method 800 advances to step 806.

STEP 806: Generating, by Segmenting the Multiphase Stack, a First Geometrical Model of a Lumen and a Second Geometrical Model of an Outer Wall of the Blood Vessel At step 806, the server 230 generates a first 3D geometrical model of the lumen of the blood vessel, and a second 3D geometrical model of the outer wall of the blood vessel by segmenting the multiphase stack.

In one embodiment, the first 3D geometrical model of the lumen of the blood vessel, and the second 3D geometrical model of the outer wall of the blood vessel are generated based on the first phase of the multiphase stack, corresponding to a time in the cardiac cycle identified as phase 0.

The method 800 advances to step 806.

STEP 808: Smoothing and Discretizing the First Geometrical Model to Obtain a Volume Mesh of the Lumen, and the Second Geometrical Model to Obtain a Surface Mesh of the Outer Wall At step 808, the server 230 smooths the first geometrical model or the 3D geometrical model of the lumen to obtain a volume mesh of the 3D geometrical model of the lumen. In one embodiment, the server 230 generates the volume mesh of the 3D geometrical model of the lumen with a top-down approach by means of the octree method.

The server 230 smooths the 3D geometrical model of the outer wall to obtain a surface mesh of the 3D geometrical model of the outer wall. In one embodiment, the surface mesh of the 3D geometrical model of the outer wall is in the form of discretized geometry of small triangular elements.

It should be noted that the smoothing of the first geometrical model to obtain the volume mesh of the lumen, and the smoothing of the second geometrical model to obtain a surface mesh of the outer wall may be executed in parallel or in sequence.

The method 800 advances to step 810

STEP 810: Calculating, Based on the Volume and the Surface Mesh, a Thickness Parameter At step 808, the server 230 calculates a thickness parameter based on the surface mesh of the outer wall and the volume mesh of the lumen. In one embodiment, the server 230 first determines a surface mesh of the lumen based on the volume mesh of the lumen. In one embodiment, the thickness parameter includes intraluminal thrombus (ILT) thickness measurements. The server 230 determines the ILT thickness based on the distance between: the outer wall surface mesh and the lumen surface mesh. In one embodiment, if there is enough resolution to discriminate between the interface between the ILT surface and the interior surface of the wall, the server 230 determines a thickness parameter based on the distance between the interior surface of the wall and the exterior surface of the wall.

It should be noted that step 810 may be executed at any time after step 806 and before step 818.

The method 800 advances to step 812.

STEP 812: Determining a Local Deformation at Each Phase of the Multiphase Stack by Mapping Voxels of the Surface Mesh to the Multiphase Stack At step 810, the server 230 determines a local deformation at each phase of the multiphase stack by mapping voxels of the surface mesh of the outer wall to the multiphase stack. In one embodiment, the server 230 uses continuum mechanics techniques to obtain a deformation gradient tensor at each phase from the deformed mesh of the outer wall.

The method 800 advances to step 814.

STEP 814: calculating, based on the local deformation at each phase, a wall strain parameter At step 814, the server 230 calculates a wall strain parameter or maximum principal strain calculation at every phase along the principal strain direction based on the deformation gradient tensor at each phase.

The method 800 advances to step 816.

STEP 816: Generating a Blood Flow Parameter Based at Least in Part on the Volume Mesh of the Lumen In one embodiment, at step 816, the server 230 first generates a simulation of blood flow in the lumen based at least in part on the volume mesh. To generate the simulation of blood flow in the lumen, the server 230 uses CFD parameters including boundary conditions, viscosity, density, and time step. The server 230 obtains the blood flow parameter, the blood flow parameter comprising a respective set of blood flow values in the lumen for a cardiac cycle. In one embodiment step 816 can be replaced by using 4D-flow MRI for a given patient: the server 230 uses 4D-flow MRI data to obtain the blood flow parameter, the blood flow parameter comprising a respective set of blood flow values in the lumen for a cardiac cycle.

In one embodiment, at step 816, the server 230 generates the blood flow parameter by performing a 4D-flow MRI. Based on the volume mesh of the 3D geometrical model of the lumen the velocity field is measured. The 4D-flow MRI may be performed by using the medical imaging apparatus 210 in instances where the medical imaging apparatus 210 is a MRI operable to perform 4D-flow MRI acquisition, or by using a MRI operable to perform 4D-flow MRI acquisition in instances where the medical imaging apparatus 210 is not a MRI.

The blood flow parameter comprises a respective set of blood flow values in the lumen for a cardiac cycle.

The method 800 advances to step 818.

STEP 818: Determining, Based on the Blood Flow Parameter, a Wall Shear Stress Parameter At step 818, the server 230 determines, based on the blood flow parameter comprising the respective set of blood flow values in the lumen for a cardiac cycle, wall shear stress (WSS) disturbances based on the CFD results to calculate a wall shear stress parameter.

The server 230 derives all-shear stress based hemodynamic wall descriptors (HWD) from the CFD results. In one embodiment, the server 230 derives all-shear stress based hemodynamic wall descriptors (HWD) from 4D-flow MRI data as alternative to CFD results. The HWD incorporate temporal variation of the magnitude and direction of the WSS vector. The server 230 calculates the wall shear stress parameter based on the HWD.

In one embodiment, the wall shear stress parameter comprises a time averaged wall-shear stress (TAWSS).

The method 800 advances to step 820.

STEP 820: Calculating, Based on: The Thickness Parameter, the Wall Strain Parameter, and the Wall Shear Stress Parameter, a Rupture Potential Parameter of the Blood Vessel At step 820, the server 230 calculates, based on the thickness parameter, the wall strain parameter, and the wall shear stress parameter, a rupture potential parameter.

In one embodiment, the server 230 defines a plurality of patches on the vessel geometries of the outer wall and the lumen perpendicularly to the lumen centerline and determines a patch-averaged distribution for each of the wall strain parameter, the thickness parameter, and the wall shear stress parameter.

In one embodiment, the server 230 receives population-based values of the wall strain parameter, the thickness parameter, and the wall shear stress parameter.

In one embodiment, the server 230 determines distribution quartiles of the patch-averaged distribution of: the ILT thickness, the wall strain, and the wall shear stress in the patch-averaged thickness parameter, the patch-averaged wall strain parameter, and the patch-averaged wall shear stress parameter respectively. In one embodiment, the distribution quartiles are determined for each patch-averaged distribution of the patient specific distribution and the population-based distribution.

In one embodiment, the server 230 classifies, for each patch, the ILT thickness, the wall strain and the wall shear stress based on the determined distribution quartiles.

In one embodiment, the server 230 assigns a category from 1 to 4 to each value in the patch-averaged thickness parameter, the patch-averaged wall strain parameter, and the patch-averaged wall shear stress parameter.

The server 230 determines, a regional rupture potential (RRP) for each patch based on the categories of patch-averaged thickness parameter, the patch-averaged wall strain parameter, and the patch-averaged wall shear stress parameter.

The regional rupture potential parameter is indicative of a state of weakening and rupture potential of each patch of the plurality of patches on the blood vessel.

The method 800 then ends.

Experimental Results

With reference to FIG. 4A to FIG. 7, there are described experimental results of determining a regional rupture potential of a patient in accordance with non-limiting embodiments of the present technology.

The patient is a 62-year old male patient with infrarenal AAA (diameter 5.6 cm), where preoperatory ECG-gated dynamic computed tomography scans showed radiographic evidence of active rupturing aneurysm, enabling to determine a regional rupture potential.

The predicted flow pattern was characterized by recirculation and low velocities at the aneurysmal sac where low TAWSS values and thick ILT predominated as depicted in FIG. 5 and FIG. 6A to 6C. A strong negative correlation was found between region-averaged TAWSS and ILT thickness ($\rho=-0.78$, $p=5.9e-06$). The main flow channel associated with high velocity was visible in the neck and in areas of impingement on the aortic wall where it resulted in high TAWSS, almost no ILT and high strain, as depicted in FIG. 5 and FIG. 6A to 6C, pointing out a moderate positive correlation between region-averaged TAWSS and maximum principal strain ($\rho=0.60$, $p=0.0022$), and between region-averaged ILT and strain ($\rho=-0.61$, $p=0.0014$).

The AAA rupture was identified at the time of operative intervention and occurred left postero-laterally at around 5 o'clock on the clock face, at the level of patch LP5 and not the location of maximum diameter, as depicted in FIG. 4A and FIG. 4B. This region presented low patch-averaged TAWSS, thick ILT and high maximum principal strain, corresponding to an RRP indicating a weak wall, as depicted in FIG. 7. Table I, reproduced above, shows all the patches with corresponding category for each descriptor: patch LP5 was assigned category 1 for TAWSS (low TAWSS), category 4 for ILT (thick thrombus) and 3 for strain (high deformability).

DISCUSSION AND CONCLUSION

The aneurysm rupture occurred at a site of reduced blood flow velocity, characterized by recirculation associated with low TAWSS and thick thrombus deposition in agreement with previously reported findings. Although the shear stress is unlikely to be the direct cause of rupture, a strong correlation found between patch-averaged TAWSS and ILT suggests a mechanism of thrombus deposition at locations of disturbed flow where low oscillatory wall shear stress predominates. The effect of ILT accumulation may contribute to local inflammatory processes and hypoxia leading to adverse remodeling and loss of structural integrity behind disease progression.

The heterogeneous remodeling is reflected in the local in vivo measurement of deformability. A moderate regional correlation between TAWSS and strain was found, as possible consequence of main flow channel impingement (neck, LA3, RA3, LA6). The ruptured patch, however, exhibited an opposite trend, showing low TAWSS and high maximum principal strain resulting in a high RRP index as indication of localized weakening, as depicted in FIG. 6A to FIG. 7. These observations allowed for a good prediction of the rupture location by adding information on the state of regional weakening of the wall. This study was limited to one ruptured patient and assumed a rigid aortic wall for CFD simulations. Despite limitations, results point out the importance of local descriptors in assessing aortic wall vulnerability and show the predictive power of combined fluid dynamic and strain analysis in estimating the rupture potential of individual aneurysms with possible clinical applications.

It should be apparent to those skilled in the art that at least some embodiments of the present technology aim to expand a range of technical solutions for addressing a particular technical problem, namely determining in vivo rupture potential of a blood vessel by using a 3D models of the blood vessel and computational fluid dynamics simulation, which may enable save computational resources.

It should be expressly understood that not all technical effects mentioned herein need to be enjoyed in each and every embodiment of the present technology. For example, embodiments of the present technology may be implemented without the user enjoying some of these technical effects, while other non-limiting embodiments may be implemented with the user enjoying other technical effects or none at all.

Some of these steps and signal sending-receiving are well known in the art and, as such, have been omitted in certain portions of this description for the sake of simplicity. The signals can be sent-received using optical means (such as a fiber-optic connection), electronic means (such as using wired or wireless connection), and mechanical means (such as pressure-based, temperature based or any other suitable physical parameter based).

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A computer-implemented method for determining a rupture potential indicative of a state of weakening of at least one region of a blood vessel of a given subject, the method being executed by a server, the method comprising:
    receiving, by the server, a plurality of images of the blood vessel of the given subject, the plurality of images having been acquired by a medical imaging apparatus;
    organizing, by the server, the plurality of images into a multiphase stack, a given phase of the multiphase stack being representative of the blood vessel at a given time in a cardiac cycle;
    generating, by the server, a volume mesh of a lumen of the blood vessel, a surface mesh of the lumen of the blood vessel and a surface mesh of an outer wall of the blood vessel, using the multiphase stack;
    calculating, by the server, based on the surface mesh of the lumen and the surface mesh of the outer wall, a thickness parameter;
    determining, by the server, a local deformation at each phase of the multiphase stack by mapping voxels of the surface mesh of the outer wall to the multiphase stack;
    calculating, by the server, based on the local deformation at each phase, a wall strain parameter indicative of a maximum principal strain at the outer wall;
    generating a blood flow parameter based at least in part on the volume mesh of the lumen, the blood flow parameter comprising a respective set of blood flow values in the lumen for a cardiac cycle;
    calculating, by the server, based on the blood flow parameter, a wall shear stress parameter indicative of wall shear disturbances in the lumen; and
    determining, by the server, based on the thickness parameter, the wall strain parameter, and the wall shear stress parameter, a rupture potential parameter of the blood vessel, the rupture potential parameter being indicative of a state of weakening of the at least one region of the blood vessel.

2. The method of claim 1, wherein the generating the blood flow parameter comprises one of:
    generating a computational flow dynamics (CFD) simulation of blood flow in the lumen to obtain the respective set of blood flow values in the lumen for the cardiac cycle; and
    performing a 4D-flow MRI acquisition to obtain the respective set of blood flow values in the lumen for the cardiac cycle.

3. The method of claim 1, wherein
    the method further comprises, prior to calculating the wall strain parameter:
        determining, based on each phase of the multiphase stack and the surface mesh of the outer wall, a local deformation at each phase of the surface mesh; and wherein
    the calculating the wall strain parameter is based on the local deformation at each phase of the surface mesh.

4. The method of claim 1, wherein the calculating the thickness parameter comprises calculating an intraluminal thrombus (ILT) thickness based on: a distance between the surface mesh of the outer wall and the surface mesh of the lumen.

5. The method of claim 1, wherein
    the method further comprises prior to the determining the rupture potential parameter:
        receiving a population-based thickness parameter, a population-based wall strain parameter, and a population-based wall shear stress parameter; and wherein
    the determining the rupture potential parameter is further based on the population-based thickness parameter, the population-based wall strain parameter, and the population-based wall shear stress parameter.

6. The method of claim 1, wherein
    the method further comprises, prior to the estimating the rupture potential parameter:
        defining, by the server, a plurality of patches on the blood vessel; wherein
        the calculating the thickness parameter, the wall strain parameter, and the wall shear stress parameter, comprises calculating a patch-averaged thickness parameter, a patch-averaged wall strain parameter and a patch-averaged wall shear stress parameter using the plurality of patches; and wherein
    the rupture potential parameter is based on the patch-averaged thickness parameter, the patch-averaged wall strain parameter and the patch-averaged wall shear stress parameter.

7. The method of claim 6, wherein the calculating the patch-averaged thickness parameter, the patch-averaged wall strain parameter and the patch-averaged wall shear stress parameter is further based on the population-based thickness parameter, the population-based wall strain parameter, and the population-based wall shear stress parameter.

8. The method of claim 7, further comprising determining respective distribution quartiles for each of the patch-averaged thickness parameter, the patch-averaged wall strain parameter and the patch-averaged wall shear stress parameter.

9. The method of claim 8, further comprising: classifying each of the patch-averaged thickness parameter, the patch-averaged wall strain parameter and the patch-averaged wall shear stress parameter based on the respective distribution quartiles.

10. The method of claim 1, wherein the rupture potential parameter is determined based on:

$$RRP = \frac{[ILT_{category} + STRAIN_{category} + (5 - TAWSS_{category})] - 3}{9} \cdot 100$$

where $ILT_{category}$ is a respective category assigned to the thickness parameter,
$STRAIN_{category}$ is a respective category assigned to the wall strain parameter, and
$TAWSS_{category}$ is a respective category assigned to the wall shear stress parameter.

11. A system for determining a rupture potential indicative of a state of weakening of at least one region of a blood vessel of a given subject, the system comprising:
a processor;
a computer-readable storage medium connected to the processor, the computer-readable storage medium including instructions;
the processor, upon executing the instructions, being configured for:
receiving a plurality of images of the blood vessel of the given subject, the plurality of images having been acquired by a medical imaging apparatus;
organizing the plurality of images into a multiphase stack, a given phase of the multiphase stack being representative of the blood vessel at a given time in a cardiac cycle;
generating a volume mesh of a lumen of the blood vessel, a surface mesh of the lumen of the blood vessel and a surface mesh of an outer wall of the blood vessel, using the multiphase stack;
calculating based on the volume mesh of the lumen and the surface mesh of the outer wall, a thickness parameter;
determining a local deformation at each phase of the multiphase stack by mapping voxels of the surface mesh of the outer wall to the multiphase stack;
calculating based on the local deformation at each phase, a wall strain parameter indicative of a maximum principal strain at the outer wall;
generating a blood flow parameter based at least in part on the volume mesh of the lumen, the blood flow parameter comprising a respective set of blood flow values in the lumen for a given moment in time;
calculating based on the blood flow parameter, a wall shear stress parameter indicative of wall shear disturbances in the lumen;
determining based on the thickness parameter, the wall strain parameter, and the wall shear stress parameter, a rupture potential parameter of the blood vessel, the rupture potential parameter being indicative of a state of weakening of at least one region of the blood vessel.

12. The system of claim 11, wherein the generating the blood flow parameter comprises one of:
generating a computational flow dynamics (CFD) simulation of blood flow in the lumen to obtain the respective set of blood flow values in the lumen for the cardiac cycle; and
performing a 4D-flow MRI acquisition to obtain the respective set of blood flow values in the lumen for the cardiac cycle.

13. The system of claim 11, wherein the processor is further configured for, prior to the calculating the wall strain parameter:
determining, based on each phase of the multiphase stack and the surface mesh of the outer wall, a local deformation at each phase of the surface mesh; and wherein
the calculating the wall strain parameter is based on the local deformation at each phase of the surface mesh.

14. The system of claim 11, wherein the thickness parameter is determined based on: a distance between the surface mesh of the outer wall and the surface mesh of the lumen.

15. The system of claim 11, wherein the processor is further configured for, prior to the determining the regional rupture potential parameter:
receiving a population-based thickness parameter, a population-based wall strain parameter, and a population-based wall shear stress parameter; and wherein
the determining the regional rupture potential parameter is further based on the population-based thickness parameter, the population-based wall strain parameter, and the population-based wall shear stress parameter.

16. The system of claim 11, wherein the processor is further configured for, prior to the estimating the rupture potential parameter:
defining a plurality of patches on the blood vessel; wherein
the calculating the thickness parameter, the wall strain parameter, and the wall shear stress parameter, comprises calculating a patch-averaged thickness parameter, a patch-averaged wall strain parameter and a patch-averaged wall shear stress parameter using the plurality of patches; and wherein
the regional rupture potential parameter is based on the patch-averaged thickness parameter, the patch-averaged wall strain parameter and the patch-averaged wall shear stress parameter.

17. The system of claim 16, wherein the calculating the patch-averaged thickness parameter, the patch-averaged wall strain parameter and the patch-averaged wall shear stress parameter is further based on the population-based thickness parameter, the population-based wall strain parameter, and the population-based wall shear stress parameter.

18. The system of claim 17, wherein the processor is further configured for determining respective distribution quartiles for each of the patch-averaged thickness parameter, the patch-averaged wall strain parameter and the patch-averaged wall shear stress parameter.

19. The system of claim 18, wherein the processor is further configured for classifying each of the patch-averaged thickness parameter, the patch-averaged wall strain parameter and the patch-averaged wall shear stress parameter based on the respective distribution quartiles.

20. The system of claim 11, wherein the rupture potential parameter is determined based on:

$$RRP = \frac{[ILT_{category} + STRAIN_{category} + (5 - TAWSS_{category})] - 3}{9} \cdot 100$$

where $ILT_{category}$ is a respective category assigned to the thickness parameter,
$STRAIN_{category}$ is a respective category assigned to the wall strain parameter, and
$TAWSS_{category}$ is a respective category assigned to the wall shear stress parameter.

* * * * *